United States Patent
Benting et al.

(10) Patent No.: US 8,372,982 B2
(45) Date of Patent: Feb. 12, 2013

(54) FUNGICIDAL N-(PHENYLCYCLOALKYL)CARBOXAMIDE, N-(BENZYLCYCLOALKYL)CARBOXAMIDE AND THIOCARBOXAMIDE DERIVATIVES

(75) Inventors: Jurgen Benting, Leichlingen (DE); Peter Dahmen, Neuss (DE); Philippe Desbordes, Lyons (FR); Stephanie Gary, Champagne au Mont d'Or (FR); Marie-Claire Grosjean-Cournoyer, Curis-au-Mont-d'Or (FR); Philippe Rinolfi, Chatillon d'Azergues (FR); Ulrike Wachendorff-Neumann, Neuwied (DE)

(73) Assignee: Bayer Cropscience AG (DE)

( * ) Notice: Subject to any disclaimer, the term of this patent is extended or adjusted under 35 U.S.C. 154(b) by 0 days.

(21) Appl. No.: 13/201,616

(22) PCT Filed: Feb. 16, 2010

(86) PCT No.: PCT/EP2010/051886
§ 371 (c)(1),
(2), (4) Date: Aug. 15, 2011

(87) PCT Pub. No.: WO2010/094666
PCT Pub. Date: Aug. 26, 2010

(65) Prior Publication Data
US 2011/0306646 A1     Dec. 15, 2011

(30) Foreign Application Priority Data

Feb. 17, 2009 (EP) ..................... 09356011
Sep. 23, 2009 (EP) ..................... 09356054

(51) Int. Cl.
| C07D 207/32 | (2006.01) |
| C07D 231/12 | (2006.01) |
| C07D 233/64 | (2006.01) |
| C07D 249/04 | (2006.01) |
| C07D 261/08 | (2006.01) |
| C07D 263/32 | (2006.01) |
| C07D 275/03 | (2006.01) |
| C07D 277/22 | (2006.01) |
| C07D 285/08 | (2006.01) |
| C07D 307/38 | (2006.01) |
| C07D 333/06 | (2006.01) |

(52) U.S. Cl. ........ 548/128; 548/200; 548/206; 548/215; 548/255; 548/267.8; 548/341.5; 548/374.1; 548/530; 549/70; 549/483

(58) Field of Classification Search .................. 548/206, 548/215, 255, 262.2, 300.1, 356.1, 400, 128, 548/200, 267.8, 341.5, 374.1, 530; 549/70, 549/483
See application file for complete search history.

(56) References Cited

FOREIGN PATENT DOCUMENTS

| WO | WO 98/03495 | 1/1998 |
| WO | WO 2005/103006 | 11/2005 |
| WO | WO 2006/122955 | 11/2006 |
| WO | WO 2007/134799 | 11/2007 |
| WO | WO-2007134799 A1 * | 11/2007 |
| WO | WO 2009/012998 | 1/2009 |

OTHER PUBLICATIONS

International Search Report issued Nov. 8, 2010 in corresponding International Application No. PCT/EP2010/051886.

* cited by examiner

Primary Examiner — Kamal Saeed
Assistant Examiner — Janet L Coppins
(74) Attorney, Agent, or Firm — Ostrolenk Faber LLP

(57) ABSTRACT

The present invention relates to a N-(Phenylcycloalkyl)carboxamide or N-(Benzylcycloalkyl)carboxamide or its thiocarboxamide derivative of formula (I) wherein A represents a carbo-linked, unsaturated or partially saturated, substituted or non-substituted 5-membered heterocyclyl group, T represents an oxygen or a sulphur atom, B represents a non aromatic carbocycle that can be substituted by one to four $C_1$-$C_8$-alkyl groups, and X, $Z^1$, $Z^2$ and $Z^3$ represent various substituents; their process of preparation; the preparation of intermediate compounds; their use as fungicide active agents, particularly in the form of fungicide compositions and methods for the control of phytopathogenic fungi, notably of plants, using these compounds or compositions.

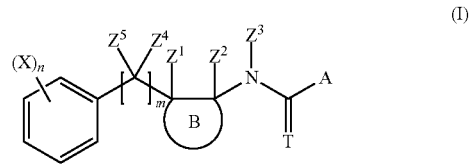

19 Claims, No Drawings

FUNGICIDAL N-(PHENYLCYCLOALKYL)CARBOXAMIDE, N-(BENZYLCYCLOALKYL)CARBOXAMIDE AND THIOCARBOXAMIDE DERIVATIVES

CROSS-REFERENCE TO RELATED APPLICATION(S)

The present application is a 35 U.S.C. §371 national phase conversion of PCT/EP2010/051886 filed Feb. 16, 2010, which claims priority of European Application No. 09356011.8 filed Feb. 17, 2009 and European Application No. 09356054.8 filed Sep. 23, 2009. Applicants claim priority to each of the foregoing patent applications. The PCT International Application was published in the English language.

The present invention relates to fungicidal N-(Phenylcycloalkyl)carboxamide or N-(Benzylcycloalkyl)carboxamide or its thiocarboxamide derivatives, their process of preparation and intermediate compounds for their preparation, their use as fungicides, particularly in the form of fungicidal compositions and methods for the control of phytopathogenic fungi of plants using these compounds or their compositions.

In international patent application WO-1998/03495, certain fungicidal N-(Phenylcyclohexyl)carboxamide derivatives are generically embraced in a broad disclosure of numerous compounds of the following formula:

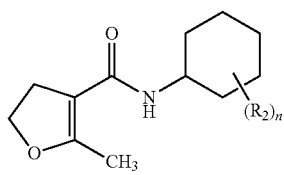

wherein $R_2$ can represent a substituted aryl group or a substituted aralkyl group and n can be 1. However, this document does not disclose compounds wherein the nitrogen atom of the carboxamide residue can be substituted by a cycloalkyl group.

In international patent application WO-2007/134799 certain fungicidal N-(Phenylcyclopropyl) (thio)carboxamide derivatives are generically embraced in a broad disclosure of numerous compounds of the following formula:

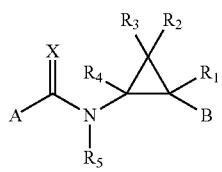

wherein A can represent a 5-membered heterocyclic ring, X can be an oxygen or sulfur atom, $R_1$, $R_2$, $R_3$ and $R_4$ can represent a hydrogen atom, a halogen atom, a $C_1$-$C_4$-alkyl, a cyano or a nitro group, B can represent a substituted phenyl group and $R_5$ can represent various substituents among which a hydrogen atom or a $C_1$-$C_4$-alkyl group. However, this document does not disclose compounds wherein the nitrogen atom of the (thio)carboxamide residue can be substituted by a cycloalkyl group.

In international patent application WO-2006/122955 certain fungicidal N-(2-Pyridylcycloalkyl) carboxamide derivatives are generically embraced in a broad disclosure of numerous compounds of the following formula:

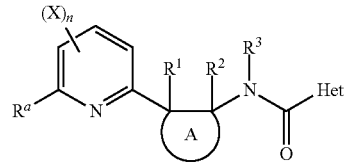

wherein Het can represent a 5-membered heterocyclic ring, A can represent a $C_3$-$C_7$-cycloalkyl ring, $R^1$ and $R^2$ can represent various substituents among which a hydrogen atom or a $C_1$-$C_6$-alkyl group, $R^3$ can represent various substituents among which a hydrogen atom, a $C_1$-$C_6$-alkyl group or a $C_3$-$C_7$-cycloalkyl group, and, X and $R^a$, the same or different, can represent various substituents among which a hydrogen atom, a halogen atom or a $C_1$-$C_3$-alkyl group. However, this document does not disclose compounds wherein the 2-pyridine moeity can be replaced by a phenyl group. Furthermore, there is no explicit disclosure in this document of any compound including a cycloalkyl group linked to the nitrogen atom of the carboxamide residue.

In international patent application WO-2005/103006 certain fungicidal N-(2-Pyridylcycloalkyl) carboxamide derivatives are generically embraced in a broad disclosure of numerous compounds of the following formula:

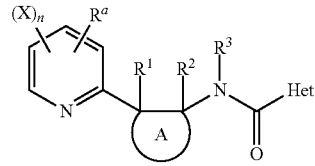

wherein Het can represent a 5-membered heterocyclic ring, A can represent a $C_3$-$C_7$-cycloalkyl ring, $R^1$ and $R^2$ can represent various substituents among which a hydrogen atom or a $C_1$-$C_6$-alkyl group, $R^3$ can represent various substituents among which a hydrogen atom, a $C_1$-$C_6$-alkyl group or a $C_3$-$C_7$-cycloalkyl group, $R^a$ represents a $C_1$-$C_6$-halogenoalkyl group and X can represent a hydrogen atom, a halogen atom, a $C_1$-$C_6$-alkyl group or a $C_1$-$C_6$-halogenoalkyl group. However, this document does not disclose compounds wherein the 2-pyridine moeity can be replaced by a phenyl group. Furthermore, there is no explicit disclosure in this document of any compound including a cycloalkyl group linked to the nitrogen atom of the carboxamide residue.

In international patent application WO-2009/016218 certain fungicidal N-cycloalkyl-N-bicyclic amides are generically embraced in a broad disclosure of numerous compounds of the following formula:

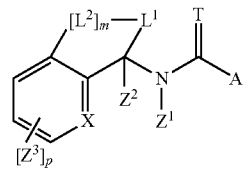

wherein A can represent a 5-membered heterocyclic ring, T can be an oxygen or sulfur atom, $Z^1$ can represent a $C_3$-$C_7$- cycloalkyl ring, $Z^2$ can represent various substituents among which a hydrogen atom or a $C_1$-$C_6$-alkyl group, $L^1$ or $L^2$ can represent various linkers among which a non-substituted or substituted $CH_2$, m can represent 1, 2 or 3 and X can represent a non-substituted or substituted CH or N. However, this document does not disclose compounds wherein the phenyl or the 2-pyridinyl moiety can be detached from the 5-, 6- or 7-membered cycloalkyl moeity.

In international patent application WO-2009/012998 certain fungicidal N-Phenyloxy-cycloalkylcarboxamide derivatives are generically embraced in a broad disclosure of numerous compounds of the following formula:

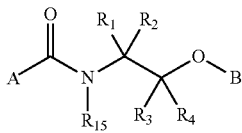

wherein A can represent a 5-membered heterocyclic ring, $R_1$, $R_2$, $R_3$ and $R_4$ can represent various substituents among which a hydrogen atom or a $C_1$-$C_4$-alkyl group and $R_1$ and $R_3$ together with the carbon to which they are linked can form a $C_3$-$C_7$-cycloalkyl ring that can be substituted by one or more $C_1$-$C_6$-alkyl groups, B can represent a substituted phenyl group and $R_{15}$ can be a hydrogen atom or a $C_3$-$C_7$-cycloalkyl group. However, this document does not disclose nor suggest compounds wherein the oxygen atom linking the B ring to the $C_3$-$C_7$-cycloalkyl moeity can be replaced by a carbon atom.

It is always of high-interest in the field of agrochemicals to use pesticidal compounds more active than the compounds already known by the man ordinary skilled in the art whereby reduced amounts of compound can be used whilst retaining equivalent efficacy. Furthermore, the provision of new pesticidal compounds with a higher efficacy strongly reduces the risk of appearance of resistant strains in the fungi to be treated. We have now found a new family of compounds which show enhanced fungicidal activity over the general known family of such compounds.

Accordingly, the present invention provides a N-(Phenylcycloalkyl)carboxamide or N-(Benzylcycloalkyl)carboxamide or its thiocarboxamide derivative of formula (I)

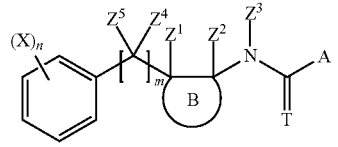

wherein
A represents a carbo-linked, unsaturated or partially saturated, 5-membered heterocyclyl group that can be substituted by up to four groups R;
T represents O or S;
B represents a 3-, 4-, 5-, 6- or 7-membered non aromatic carbocycle that can be substituted by one to four $C_1$-$C_8$-alkyl groups;
n represents 0, 1, 2, 3, 4 or 5;
m represents 0 or 1;
X represents a halogen atom; nitro; cyano; isonitrile; hydroxy; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-halogenoalkyl having 1 to 5 halogen atoms; substituted or non-substituted $C_2$-$C_8$-alkenyl; $C_2$-$C_8$-halogenoalkenyl having 1 to 5 halogen atoms; substituted or non-substituted $C_2$-$C_8$-alkynyl; $C_2$-$C_8$-halogenoalkynyl having 1 to 5 halogen atoms; substituted or non-substituted $C_1$-$C_8$-alkoxy; $C_1$-$C_8$-halogenoalkoxy having 1 to 5 halogen atoms; substituted or non-substituted $C_1$-$C_8$-alkylsulfanyl; $C_1$-$C_8$-halogenoalkylsulfanyl having 1 to 5 halogen atoms; substituted or non-substituted $C_1$-$C_8$-alkylsulfinyl; $C_1$-$C_8$-halogenoalkylsulfinyl having 1 to 5 halogen atoms; substituted or non-substituted $C_1$-$C_8$-alkylsulfonyl; $C_1$-$C_8$-halogenoalkylsulfonyl having 1 to 5 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-halogenoalkenyloxy having 1 to halogen atoms; substituted or non-substituted $C_3$-$C_8$-alkynyloxy; $C_2$-$C_8$-halogenoalkynyloxy having 1 to 5 halogen atoms; substituted or non-substituted $C_3$-$C_7$-cycloalkyl; $C_3$-$C_7$-halogenocycloalkyl having 1 to 5 halogen atoms; substituted or non-substituted ($C_3$-$C_7$-cycloalkyl)-$C_1$-$C_8$-alkyl; substituted or non-substituted ($C_3$-$C_7$-cycloalkyl)-$C_2$-$C_8$-alkenyl; substituted or non-substituted ($C_3$-$C_7$-cycloalkyl)-$C_2$-$C_8$-alkynyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted $C_1$-$C_8$-alkylcarbonyl; $C_1$-$C_8$-halogenoalkylcarbonyl having 1 to 5 halogen atoms; substituted or non-substituted $C_1$-$C_8$-alkylcarbonyloxy; $C_1$-$C_8$-halogenoalkylcarbonyloxy having 1 to 5 halogen atoms; substituted or non-substituted $C_1$-$C_8$-alkylcarbonylamino; $C_1$-$C_8$-halogenoalkyl-carbonylamino having 1 to 5 halogen atoms; substituted or non-substituted $C_1$-$C_8$-alkoxycarbonyl; $C_1$-$C_8$-halogenoalkoxycarbonyl having 1 to 5 halogen atoms; substituted or non-substituted $C_1$-$C_8$-alkylxycarbonyloxy; $C_1$-$C_8$-halogenoalkoxycarbonyloxy having 1 to 5 halogen atoms; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl that can be substituted by up to 6 groups Q; $C_1$-$C_8$-arylalkyl that can be substituted by up to 6 groups Q; $C_2$-$C_8$-arylalkenyl that can be substituted by up to 6 groups Q; $C_2$-$C_8$-arylalkynyl that can be substituted by up to 6 groups Q; aryloxy that can be substituted by up to 6 groups Q; arylsulfanyl that can be substituted by up to 6 groups Q; arylamino that can be substituted by up to 6 groups Q; $C_1$-$C_8$-arylalkyloxy that can be substituted by up to 6 groups Q; $C_1$-$C_8$-arylalkylsulfanyl that can be substituted by up to 6 groups Q; or $C_1$-$C_8$-arylalkylamino that can be substituted by up to 6 groups Q;
two substituents X together with the consecutive carbon atoms to which they are linked can form a 5- or 6-membered, saturated carbocycle or saturated heterocycle, which can be substituted by up to four groups Q which can be the same or different;

$Z^1$ and $Z^2$ independently represent a hydrogen atom; a halogen atom; cyano; a substituted or non-substituted $C_1$-$C_8$-alkyl; $C_1$-$C_8$-halogenoalkyl having 1 to 5 halogen atoms; substituted or non-substituted $C_1$-$C_8$-alkoxy; substituted or non-substituted $C_1$-$C_8$-alkylsulfanyl; or substituted or non-substituted $C_1$-$C_8$-alkoxycarbonyl;

$Z^3$ represents a non-substituted $C_3$-$C_7$-cycloalkyl or a $C_3$-$C_7$-cycloalkyl substituted by up to 10 atoms or groups that can be the same or different and that can be selected in the list consisting of halogen atoms, cyano, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl and di-$C_1$-$C_8$-alkylamino-carbonyl;

$Z^4$ and $Z^5$ independently represent a hydrogen atom; a halogen atom; cyano; a substituted or non-substituted $C_1$-$C_8$-alkyl; $C_1$-$C_8$-halogenoalkyl having 1 to 5 halogen atoms; substituted or non-substituted $C_1$-$C_8$-alkoxy; substituted or non-substituted $C_1$-$C_8$-alkylsulfanyl; substituted or non-substituted $C_1$-$C_8$-alkoxycarbonyl; or $Z_4$ and $Z_5$ are a $C_2$-$C_5$-alkylene group that can be substituted by one to four $C_1$-$C_8$-alkyl groups;

Q independently represents a halogen atom; cyano; nitro; substituted or non-substituted $C_1$-$C_8$-alkyl; $C_1$-$C_8$-halogenoalkyl having 1 to 9 halogen atoms that can be the same or different; substituted or non-substituted $C_1$-$C_8$-alkoxy; $C_1$-$C_8$-halogenoalkoxy having 1 to 9 halogen atoms that can be the same or different; substituted or non-substituted $C_1$-$C_8$-alkylsulfanyl; $C_1$-$C_8$-halogenoalkylsulfanyl having 1 to 9 halogen atoms that can be the same or different; substituted or non-substituted tri($C_1$-$C_8$)alkylsilyl; substituted or non-substituted tri($C_1$-$C_8$)alkylsilyl-$C_1$-$C_8$-alkyl; substituted or non-substituted ($C_1$-$C_8$-alkoxyimino)-$C_1$-$C_8$-alkyl; substituted or non-substituted (benzyloxyimino)-$C_1$-$C_8$-alkyl;

R independently represents hydrogen atom; halogen atom; nitro; cyano; hydroxy; amino; sulfanyl; pentafluoro-$\lambda^6$-sulfanyl; substituted or non-substituted ($C_1$-$C_8$-alkoxyimino)-$C_1$-$C_8$-alkyl; substituted or non-substituted (benzyloxyimino)-$C_1$-$C_8$-alkyl; substituted or non-substituted $C_1$-$C_8$-alkyl; $C_1$-$C_8$-halogenoalkyl having 1 to 5 halogen atoms; substituted or non-substituted $C_2$-$C_8$-alkenyl; $C_2$-$C_8$-halogenoalkenyl having 1 to 5 halogen atoms; substituted or non-substituted $C_2$-$C_8$-alkynyl; $C_2$-$C_8$-halogenoalkynyl having 1 to 5 halogen atoms; substituted or non-substituted $C_1$-$C_8$-alkoxy; $C_1$-$C_8$-halogenoalkoxy having 1 to 5 halogen atoms; substituted or non-substituted $C_1$-$C_8$-alkylsulfanyl; $C_1$-$C_8$-halogenoalkylsulfanyl having 1 to 5 halogen atoms; substituted or non-substituted $C_1$-$C_8$-alkylsulfinyl; $C_1$-$C_8$-halogenoalkylsulfinyl having 1 to 5 halogen atoms; substituted or non-substituted $C_1$-$C_8$-alkylsulfonyl; $C_1$-$C_8$-halogenoalkylsulfonyl having 1 to 5 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; substituted or non-substituted $C_3$-$C_8$-alkynyloxy; substituted or non-substituted $C_3$-$C_7$-cycloalkyl; $C_3$-$C_7$-halogenocycloalkyl having 1 to 5 halogen atoms; substituted or non-substituted tri($C_1$-$C_8$)alkylsilyl; substituted or non-substituted $C_1$-$C_8$-alkylcarbonyl; $C_1$-$C_8$-halogenoalkylcarbonyl having 1 to 5 halogen atoms; substituted or non-substituted $C_1$-$C_8$-alkoxycarbonyl; $C_1$-$C_8$-halogenoalkoxycarbonyl having 1 to 5 halogen atoms; substituted or non-substituted $C_1$-$C_8$-alkylcarbamoyl; substituted or non-substituted di-$C_1$-$C_8$-alkylcarbamoyl; phenoxy; phenylsulfanyl; phenylamino; benzyloxy; benzylsulfanyl; or benzylamino;

as well as its salts, N-oxydes, metallic complexes, metalloidic complexes and optically active isomers.

For the compounds according to the invention, the following generic terms are generally used with the following meanings:

halogen means fluorine, bromine, chlorine or iodine.
carboxy means —C(═O)OH;
carbonyl means —C(═O)—;
carbamoyl means —C(═O)NH$_2$;
N-hydroxycarbamoyl means —C(═O)NHOH;
SO represents a sulfoxyde group;
SO$_2$ represents a sulfone group;
an alkyl group, an alkenyl group and an alkynyl group as well as moieties containing these terms, can be linear or branched;
the aryl moiety contained in an aryl group, an arylalkyl group, an arylalkenyl group and an arylalkynyl group as well as moieties containing these terms, can be a phenyl group that can be substituted by up to 5 groups Q, a naphtyl group that can be substituted by up to 6 groups Q or a pyridyl group that can be substituted by up to 4 groups Q;
and, heteroatom means sulphur, nitrogen or oxygen.
in the case of an amino group or the amino moiety of any other amino-comprising group, substituted by two substituents that can be the same or different, the two substituents together with the nitrogen atom to which they are linked can form a heterocyclyl group, preferably a 5- to 7-membered heterocyclyl group, that can be substituted or that can include other hetero atoms, for example a morpholino group or piperidinyl group.
unless indicated otherwise, a group or a substituent that is substituted according to the invention can be substituted by one or more of the following groups or atoms: a halogen atom, a nitro group, a hydroxy group, a cyano group, an amino group, a sulfanyl group, a pentafluoro-$\lambda^6$-sulfanyl group, a formyl group, a formyloxy group, a formylamino group, a carbamoyl group, a N-hydroxycarbamoyl group, a carbamate group, a (hydroxyimino)-$C_1$-$C_6$-alkyl group, a $C_1$-$C_8$-alkyl, a tri($C_1$-$C_8$-alkyl)silyl-$C_1$-$C_8$-alkyl, $C_1$-$C_8$-cycloalkyl, tri($C_1$-$C_8$-alkyl)silyl-$C_1$-$C_8$-cycloalkyl, a $C_1$-$C_8$-halogenoalkyl having 1 to 5 halogen atoms, a $C_1$-$C_8$-halogenocycloalkyl having 1 to 5 halogen atoms, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a $C_1$-$C_8$-alkylaminosulfamoyl, a di-$C_1$-$C_8$-alkylaminosulfamoyl, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a 2-oxopyrrolidin-1-yl, (benzyloxyimino)-$C_1$-$C_6$-alkyl, $C_1$-$C_8$-alkoxyalkyl, $C_1$-$C_8$-halogenoalkoxyalkyl having 1 to 5 halogen atoms, benzyloxy, benzylsulfanyl, benzylamino, phenoxy, phenylsulfanyl, or phenylamino.

Any of the compounds of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions) and to the mixtures of all the possible stereoisomers, in all proportions. The diastereoisomers and/or the optical isomers can be separated according to the methods which are known per se by the man ordinary skilled in the art.

Any of the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

Any of the compounds of the present invention can also exist in one or more geometric isomer forms depending on the relative position (syn/anti or cis/trans) of the substituents of ring B. The invention thus relates equally to all syn/anti (or cis/trans) isomers and to all possible syn/anti (or cis/trans) mixtures, in all proportions. The syn/anti (or cis/trans) isomers can be separated according to general methods, which are known per se by the man ordinary skilled in the art. Any of the compounds of formula (I) wherein X represents a hydroxy, a sulfanyl group or an amino group may be found in its tautomeric form resulting from the shift of the proton of said hydroxy, sulfanyl or amino group. Such tautomeric forms of such compounds are also part of the present invention. More generally speaking, all tautomeric forms of compounds of formula (I) wherein X represents a hydroxy, a sulfanyl group or an amino group, as well as the tautomeric forms of the compounds which can optionally be used as intermediates in the preparation processes and which will be defined in the description of these processes, are also part of the present invention.

Preferred compounds according to the invention are compounds of formula (I) wherein A is selected in the list consisting of:
a heterocycle of formula ($A^1$)

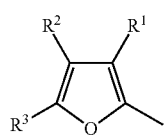

(A¹)

wherein:
$R^1$ to $R^3$ that can be the same or different represent a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or $C_1$-$C_5$-halogenoalkoxy comprising up to 9 halogen atoms that can be the same or different;
a heterocycle of formula ($A^2$)

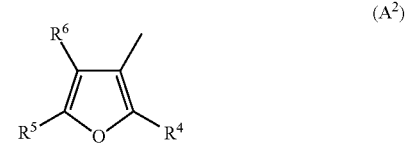

(A²)

wherein:
$R^4$ to $R^6$ that can be the same or different represent a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or $C_1$-$C_5$-halogenoalkoxy comprising up to 9 halogen atoms that can be the same or different;
a heterocycle of formula ($A^3$)

(A³)

wherein:
$R^7$ represents a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or $C_1$-$C_5$-halogenoalkoxy comprising up to 9 halogen atoms that can be the same or different;
$R^8$ represents a hydrogen atom or a substituted or non-substituted $C_1$-$C_5$-alkyl;
a heterocycle of formula ($A^4$)

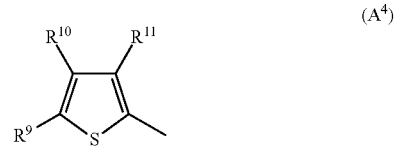

(A⁴)

wherein:
$R^9$ to $R^{11}$ that can be the same or different represent a hydrogen atom; a halogen atom; substituted or non-substituted $C_1$-$C_5$-alkyl; amino; substituted or non-substituted $C_1$-$C_5$-alkoxy; substituted or non-substituted $C_1$-$C_5$-alkylsulphanyl; $C_1$-$C_5$-halogenoalkyl comprising up to 9 halogen atoms that can be the same or different or $C_1$-$C_5$-halogenoalkoxy comprising up to 9 halogen atoms that can be the same or different;

a heterocycle of formula (A⁵)

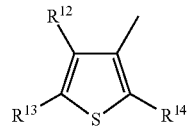

wherein:
$R^{12}$ and $R^{13}$ that can be the same or different represent a hydrogen atom; a halogen atom; substituted or non-substituted $C_1$-$C_5$-alkyl; substituted or non-substituted $C_1$-$C_5$-alkoxy; amino; $C_1$-$C_5$-halogenoalkyl comprising up to 9 halogen atoms that can be the same or different or $C_1$-$C_5$-halogenoalkoxy comprising up to 9 halogen atoms that can be the same or different;

$R^{14}$ represents a hydrogen atom; a halogen atom; substituted or non-substituted $C_1$-$C_5$-alkyl; substituted or non-substituted $C_1$-$C_5$-alkoxy; amino; $C_1$-$C_5$-halogenoalkyl comprising up to 9 halogen atoms that can be the same or different or $C_1$-$C_5$-halogenoalkoxy comprising up to 9 halogen atoms that can be the same or different;

a heterocycle of formula (A⁶)

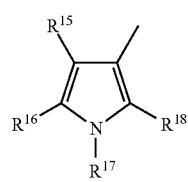

wherein:
$R^{15}$ represents a hydrogen atom; a halogen atom; a cyano; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

$R^{16}$ and $R^{18}$ that can be the same or different represent a hydrogen atom; a halogen atom; substituted or non-substituted $C_1$-$C_5$-alkoxycarbonyl; substituted or non-substituted $C_1$-$C_5$-alkyl; $C_1$-$C_5$-halogenoalkoxy comprising up to 9 halogen atoms that can be the same or different or $C_1$-$C_5$-halogenoalkyl comprising up to 9 halogen atoms that can be the same or different;

$R^{17}$ represent a hydrogen atom or substituted or non-substituted $C_1$-$C_5$-alkyl;

a heterocycle of formula (A⁷)

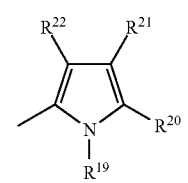

wherein:
$R^{19}$ represents a hydrogen atom or a $C_1$-$C_5$-alkyl
$R^{20}$ to $R^{22}$ that can be the same or different represent a hydrogen atom; a halogen atom; substituted or non-substituted $C_1$-$C_5$-alkyl or $C_1$-$C_5$-halogenoalkyl comprising up to 9 halogen atoms that can be the same or different;

a heterocycle of formula (A⁸)

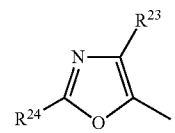

wherein:
$R^{23}$ represents a hydrogen atom; a halogen atom; substituted or non-substituted $C_1$-$C_5$-alkyl or $C_1$-$C_5$-halogenoalkyl comprising up to 9 halogen atoms that can be the same or different; $R^{24}$ represents a hydrogen atom or substituted or non-substituted $C_1$-$C_5$-alkyl or $C_1$-$C_5$-halogenoalkyl comprising up to 9 halogen atoms that can be the same or different;

a heterocycle of formula (A⁹)

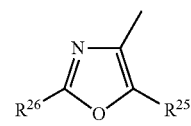

wherein:
$R^{25}$ represents a hydrogen atom; a halogen atom; substituted or non-substituted $C_1$-$C_6$-alkyl or $C_1$-$C_5$-halogenoalkyl comprising up to 9 halogen atoms that can be the same or different;

$R^{26}$ represents a hydrogen atom; substituted or non-substituted $C_1$-$C_5$-alkyl or $C_1$-$C_5$-halogenoalkyl comprising up to 9 halogen atoms that can be the same or different;

a heterocycle of formula (A¹⁰)

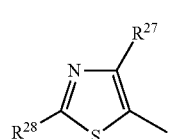

wherein:
$R^{27}$ represents a hydrogen atom; a halogen atom; substituted or non-substituted $C_1$-$C_5$-alkyl or $C_1$-$C_5$-halogenoalkyl comprising up to 9 halogen atoms that can be the same or different;

$R^{28}$ represents a hydrogen atom; a halogen atom; substituted or non-substituted $C_1$-$C_5$-alkyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or substituted or non-substituted di($C_1$-$C_5$-alkyl)amino;

a heterocycle of formula ($A^{11}$)

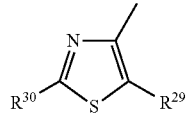

wherein:
$R^{29}$ represents a hydrogen atom; a halogen atom; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;
$R^{30}$ represents a hydrogen atom; a halogen atom; substituted or non-substituted $C_1$-$C_5$-alkyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or substituted or non-substituted di($C_1$-$C_5$-alkyl)amino;
a heterocycle of formula ($A^{12}$)

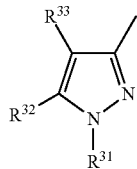

wherein:
$R^{31}$ represents a hydrogen atom or a substituted or non-substituted $C_1$-$C_5$-alkyl
$R^{32}$ represents a hydrogen atom; a halogen atom; substituted or non-substituted $C_1$-$C_5$-alkyl or $C_1$-$C_5$-halogenoalkyl comprising up to 9 halogen atoms that can be the same or different;
$R^{33}$ represents a hydrogen atom; a halogen atom; a nitro; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;
a heterocycle of formula ($A^{13}$)

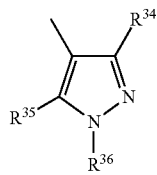

wherein:
$R^{34}$ represents a hydrogen atom; a halogen atom; substituted or non-substituted $C_1$-$C_5$-alkyl; substituted or non-substituted $C_3$-$C_5$-cycloalkyl; $C_1$-$C_5$-halogenoalkyl comprising up to 9 halogen atoms that can be the same or different; substituted or non-substituted $C_1$-$C_5$-alkoxy; substituted or non-substituted $C_2$-$C_5$-alkynyloxy or $C_1$-$C_5$-halogenoalkoxy comprising up to 9 halogen atoms that can be the same or different;
$R^{35}$ represents a hydrogen atom; a halogen atom; substituted or non-substituted $C_1$-$C_5$-alkyl; a cyano; substituted or non-substituted $C_1$-$C_5$-alkoxy; substituted or non-substituted $C_1$-$C_5$-alkylsulphanyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or substituted or non-substituted di($C_1$-$C_5$-alkyl)amino;
$R^{36}$ represents a hydrogen atom or substituted or non-substituted $C_1$-$C_5$-alkyl;
a heterocycle of formula ($A^{14}$)

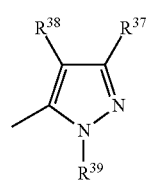

wherein:
$R^{37}$ and $R^{38}$ that can be the same or different represent a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or a substituted or non-substituted $C_1$-$C_5$-alkylsulphanyl;
$R^{39}$ represents a hydrogen atom or substituted or non-substituted $C_1$-$C_5$-alkyl;
a heterocycle of formula ($A^{15}$)

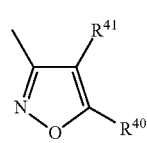

wherein:
$R^{40}$ and $R^{41}$ that can be the same or different represent a hydrogen atom; a halogen atom; substituted or non-substituted $C_1$-$C_5$-alkyl or $C_1$-$C_5$-halogenoalkyl comprising up to 9 halogen atoms that can be the same or different;
a heterocycle of formula ($A^{16}$)

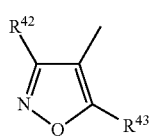

wherein:
$R^{42}$ and $R^{43}$ that can be the same or different represent a hydrogen atom; a halogen atom; substituted or non-substituted $C_1$-$C_5$-alkyl; $C_1$-$C_5$-halogenoalkyl comprising up to 9 halogen atoms that can be the same or different or amino;

a heterocycle of formula ($A^{17}$)

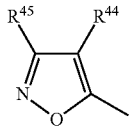

wherein:
$R^{44}$ and $R^{45}$ that can be the same or different represent a hydrogen atom; a halogen atom; substituted or non-substituted $C_1$-$C_5$-alkyl or $C_1$-$C_5$-halogenoalkyl comprising up to 9 halogen atoms that can be the same or different;

a heterocycle of formula ($A^{18}$)

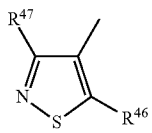

wherein:
$R^{47}$ represents a hydrogen atom; a halogen atom; substituted or non-substituted $C_1$-$C_5$-alkyl or $C_1$-$C_5$-halogenoalkyl comprising up to 9 halogen atoms that can be the same or different;
$R^{46}$ represents a hydrogen atom; a halogen atom; substituted or non-substituted $C_1$-$C_5$-alkyl; $C_1$-$C_5$-halogenoalkyl comprising up to 9 halogen atoms that can be the same or different or substituted or non-substituted $C_1$-$C_5$-alkylsulfanyl;

a heterocycle of formula ($A^{19}$)

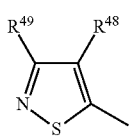

wherein:
$R^{49}$ and $R^{48}$ that can be the same or different represent a hydrogen atom; a halogen atom; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

a heterocycle of formula ($A^{20}$)

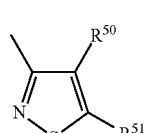

wherein:
$R^{50}$ and $R^{51}$ that can be the same or different represent a hydrogen atom; a halogen atom; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

a heterocycle of formula ($A^{21}$)

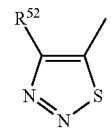

wherein:
$R^{52}$ represents a hydrogen atom; a halogen atom; substituted or non-substituted $C_1$-$C_5$-alkyl or $C_1$-$C_5$-halogenoalkyl comprising up to 9 halogen atoms that can be the same or different.

a heterocycle of formula ($A^{22}$)

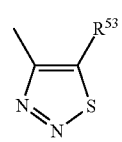

wherein:
$R^{53}$ represents a hydrogen atom; a halogen atom; substituted or non-substituted $C_1$-$C_5$-alkyl or $C_1$-$C_5$-halogenoalkyl comprising up to 9 halogen atoms that can be the same or different.

a heterocycle of formula ($A^{23}$)

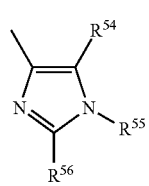

wherein:
$R^{54}$ and $R^{56}$ that can be the same or different represent a hydrogen atom; a halogen atom; substituted or non-substituted $C_1$-$C_5$-alkyl or $C_1$-$C_5$-halogenoalkyl comprising up to 9 halogen atoms that can be the same or different;
$R^{55}$ represents a hydrogen atom or substituted or non-substituted $C_1$-$C_5$-alkyl;

a heterocycle of formula ($A^{24}$)

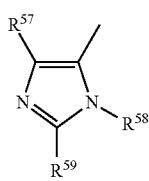

wherein:
$R^{57}$ and $R^{59}$ that can be the same or different represent a hydrogen atom; a halogen atom; substituted or non-substituted $C_1$-$C_5$-alkyl or $C_1$-$C_5$-halogenoalkyl comprising up to 9 halogen atoms that can be the same or different;
$R^{58}$ represents a hydrogen atom or substituted or non-substituted $C_1$-$C_5$-alkyl;

a heterocycle of formula ($A^{25}$)

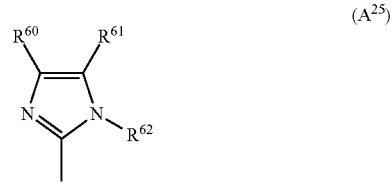

wherein:
$R^{60}$ and $R^{61}$ that can be the same or different represent a hydrogen atom; a halogen atom; substituted or non-substituted $C_1$-$C_5$-alkyl or $C_1$-$C_5$-halogenoalkyl comprising up to 9 halogen atoms that can be the same or different;
$R^{62}$ represents a hydrogen atom or substituted or non-substituted $C_1$-$C_5$-alkyl;

a heterocycle of formula ($A^{26}$)

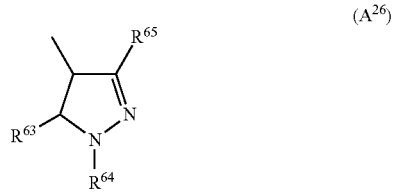

wherein:
$R^{65}$ represents a hydrogen atom; a halogen atom; substituted or non-substituted $C_1$-$C_5$-alkyl; substituted or non-substituted $C_3$-$C_5$-cycloalkyl; $C_1$-$C_5$-halogenoalkyl comprising up to 9 halogen atoms that can be the same or different; substituted or non-substituted $C_1$-$C_5$-alkoxy; substituted or non-substituted $C_2$-$C_5$-alkynyloxy or $C_1$-$C_5$-halogenoalkoxy comprising up to 9 halogen atoms that can be the same or different;
$R^{63}$ represents a hydrogen atom; a halogen atom; substituted or non-substituted $C_1$-$C_5$-alkyl; a cyano; substituted or non-substituted $C_1$-$C_5$-alkoxy; substituted or non-substituted $C_1$-$C_5$-alkylsulphanyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or di($C_1$-$C_6$-alkyl)amino;
$R^{64}$ represents a hydrogen atom or substituted or non-substituted $C_1$-$C_5$-alkyl.

More preferred compounds according to the invention are compounds of formula (I) wherein A is selected in the list consisting of $A^2$; $A^6$; $A^{10}$ and $A^{13}$ as herein-defined. Even more preferred compounds according to the invention are compounds of formula (I) wherein A represents $A^{13}$ wherein $R^{34}$ represents a substituted or non-substituted $C_1$-$C_5$-alkyl, $C_1$-$C_5$-halogenoalkyl comprising up to 9 halogen atoms that can be the same or different; substituted or non-substituted $C_1$-$C_5$-alkoxy; $R^{35}$ represents a hydrogen atom or a halogen atom and $R^{36}$ represents a substituted or non-substituted $C_1$-$C_5$-alkyl.

Other preferred compounds according to the invention are compounds of formula (I) wherein T represents O.

Other preferred compounds according to the invention are compounds of formula (I) wherein n represents 0, 1 or 2.

Other preferred compounds according to the invention are compounds of formula (I) wherein B is a 3-, 5-, 6- or 7-membered non aromatic carbocycle that can be substituted by one to four $C_1$-$C_8$-alkyl groups.

Even more preferably, B is chosen from cyclopropyl, cyclopentyl, cyclohexyl and cycloheptyl carbocycle that can be substituted by one to four methyl groups.

Other preferred compounds according to the invention are compounds of formula (I) wherein X independently represents a halogen atom; substituted or non-substituted $C_1$-$C_8$-alkyl; $C_1$-$C_8$-halogenoalkyl comprising up to 9 halogen atoms that can be the same or different; substituted or non-substituted tri($C_1$-$C_8$-alkyl)silyl; substituted or non-substituted $C_1$-$C_8$-alkoxy or $C_1$-$C_8$-halogenoalkoxy comprising up to 9 halogen atoms that can be the same or different; or wherein two consecutive substituents X together with the phenyl ring form a substituted or non substituted 1,3-benzodioxolyl; 1,2,3,4-tetrahydro-quinoxalinyl; 3,4-dihydro-2H-1,4-benzoxazinyl; 1,4-benzodioxanyl; indanyl; 2,3-dihydrobenzofuranyl; or indolinyl.

Other preferred compounds according to the invention are compounds of formula (I) wherein $Z^1$ and $Z^2$ independently represent a hydrogen atom or a substituted or non-substituted $C_1$-$C_8$-alkyl.

Other preferred compounds according to the invention are compounds of formula (I) wherein $Z^3$ represents a non-substituted $C_3$-$C_7$ cycloalkyl or a $C_3$-$C_7$ cycloalkyl substituted by up to 10 groups or atoms that can be the same or different and that can be selected in the list consisting of halogen atoms, $C_1$-$C_8$-alkyl, $C_1$-$C_8$-halogenoalkyl comprising up to 9 halogen atoms that can be the same or different, $C_1$-$C_8$-alkoxy or $C_1$-$C_8$-halogenoalkoxy comprising up to 9 halogen atoms that can be the same or different. More preferably $Z^3$ represents a non-substituted $C_3$-$C_7$-cycloalkyl; even more preferably $Z^3$ represents cyclopropyl.

Other preferred compounds according to the invention are compounds of formula (I) wherein $Z^4$ and $Z^5$ independently represent a hydrogen atom, a halogen atom or a substituted or non-substituted $C_1$-$C_8$-alkyl.

Other preferred compounds according to the invention are compounds of formula (I) wherein R independently represents a hydrogen atom; halogen atom; cyano; substituted or non-substituted $C_1$-$C_8$-alkylamino; substituted or non-substituted di-$C_1$-$C_8$-alkylamino; substituted or non-substituted tri($C_1$-$C_8$-alkyl)silyl; substituted or non-substituted $C_1$-$C_8$-alkyl; $C_1$-$C_8$-halogenoalkyl comprising up to 9 halogen atoms that can be the same or different; substituted or non-substituted $C_1$-$C_8$-alkoxy; $C_1$-$C_8$-halogenoalkoxy comprising up to 9 halogen atoms that can be the same or different; substituted or non-substituted $C_1$-$C_8$-alkylsulfanyl; amino; hydroxyl; nitro; substituted or non-substituted $C_1$-$C_8$-alkoxycarbonyl; substituted or non-substituted $C_2$-$C_8$-alkynyloxy.

The above mentioned preferences with regard to the substituents of the compounds according to the invention can be combined in various manners. These combinations of preferred features thus provide sub-classes of compounds according to the invention. Examples of such sub-classes of preferred compounds according to the invention can be combined:
preferred features of A with preferred features of B, $Z^1$, $Z^2$, $Z^3$, $Z^4$, $Z^5$, X, T, n, m and R;
preferred features of B with preferred features of A, $Z^1$, $Z^2$, $Z^3$, $Z^4$, $Z^5$, X, T, n, m and R;
preferred features of $Z^1$ with preferred features of A, B, $Z^2$, $Z^3$, $Z^4$, $Z^5$, X, T, n, m and R;

preferred features of $Z^2$ with preferred features of A, B, $Z^1$, $Z^3$, $Z^4$, $Z^5$, X, T, n, m and R;

preferred features of $Z^3$ with preferred features of A, B, $Z^1$, $Z^2$, $Z^4$, $Z^5$, X, T, n, m and R;

preferred features of $Z^4$ with preferred features of A, B, $Z^1$, $Z^2$, $Z^3$, $Z^5$, X, T, n, m and R;

preferred features of $Z^5$ with preferred features of A, B, $Z^1$, $Z^2$, $Z^3$, $Z^4$, X, T, n, m and R;

preferred features of X with preferred features of A, B, $Z^1$, $Z^2$, $Z^3$, $Z^4$, $Z^5$, T, n, m and R;

preferred features of T with preferred features of A, B, $Z^1$, $Z^2$, $Z^3$, $Z^4$, $Z^5$, X, n, m and R;

preferred features of n with preferred features of A, B, $Z^1$, $Z^2$, $Z^3$, $Z^4$, $Z^5$, X, T, m and R;

preferred features of m with preferred features of A, B, $Z^1$, $Z^2$, $Z^3$, $Z^4$, $Z^5$, X, T, n and R;

preferred features of R with preferred features of A, B, $Z^1$, $Z^2$, $Z^3$, $Z^4$, $Z^5$, X, T, n and m;

In these combinations of preferred features of the substituents of the compounds according to the invention, the said preferred features can also be selected among the more preferred features of each of A, B, $Z^1$, $Z^2$, $Z^3$, $Z^4$, $Z^5$, X, T, n, m and R, so as to form most preferred subclasses of compounds according to the invention.

The present invention also relates to a process for the preparation of the compound of formula (I).

Thus, according to a further aspect of the present invention there is provided a process P1 for the preparation of a compound of formula (I) as herein-defined and wherein T represents O and that comprises reacting a 2-phenylcycloalkylamine or 2-benzylcycloalkylamine derivative of formula (II) or one of its salts:

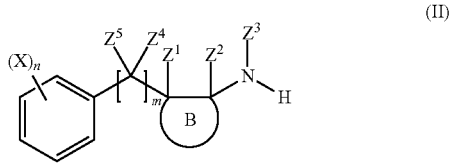

(II)

wherein X, n, m, B, $Z^1$, $Z^2$, $Z^3$, $Z^4$ and $Z^5$ are as herein-defined; with a carboxylic acid derivative of formula (III):

(III)

wherein A is as herein-defined and $L^1$ represents a leaving group selected in the list consisting of a halogen atom, a hydroxyl group, —$OR^a$, —$OC(=O)R^a$, $R^a$ being a substituted or non-substituted $C_1$-$C_6$-alkyl, a substituted or non-substituted $C_1$-$C_6$-haloalkyl, a benzyl, 4-methoxybenzyl or pentafluorophenyl group, or a group of formula O—C(=O) A; in the presence of a catalyst and in the presence of a condensing agent in case $L^1$ represents a hydroxyl group, and in the presence of an acid binder in case $L^1$ represents a halogen atom.

N-cycloalkylamine derivatives of formula (II) can be prepared by known processes such as reductive amination of aldehyde or ketone (Bioorganics and Medicinal Chemistry Letters (2006), 2014), or reduction of imines (Tetrahedron (2005), 11689), or nucleophilic substitution of halogen, mesylate or tosylate (Journal of Medicinal Chemistry (2002), 3887).

Carboxylic acid derivatives of formula (III) can be prepared by known processes.

In case $L^1$ represents a hydroxy group, the process according to the present invention is conducted in the presence of condensing agent. Suitable condensing agent may be selected in the non limited list consisting of acid halide former, such as phosgene, phosphorous tribromide, phosphorous trichloride, phosphorous-pentachloride, phosphorous trichloride oxide or thionyl chloride; anhydride former, such as ethyl chloroformate, methyl chloroformate, isopropyl chloroformate, isobutyl chloroformate or methanesulfonyl-chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquino line (EEDQ), triphenylphosphine/tetrachloro-methane, dimethoxy[1.3.5]triazin-2-yl)-4-methylmorpholinium chloride hydrate or bromo-tripyrrolidino-phosphonium-hexafluorophosphate.

The process according to the present invention is conducted in the presence of a catalyst. Suitable catalyst may be selected in the list consisting of 4-dimethyl-aminopyridine, 1-hydroxy-benzotriazole or dimethylformamide.

In case $L^1$ represents a halogen atom, the process according to the present invention is conducted in the presence of an acid binder. Suitable acid binders for carrying out process P1 according to the invention are in each case all inorganic and organic bases that are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as cesium carbonate, sodium carbonate, potassium carbonate, potassium bicarbonate, sodium bicarbonate, alkali metal or alkaline earth metal acetates, such as sodium acetate, potassium acetate, calcium acetateand also tertiary amines, such as trimethylamine, triethylamine, diisopropylethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

It is also possible to work in the absence of an additional condensing agent or to employ an excess of the amine component, so that it simultaneously acts as acid binder agent.

According to a further aspect according to the invention, there is provided a process P2 for the preparation of a compound of formula (I) wherein T represents S, starting from a compound of formula (I) wherein T represents O and illustrated according to the following reaction scheme:

Process P2

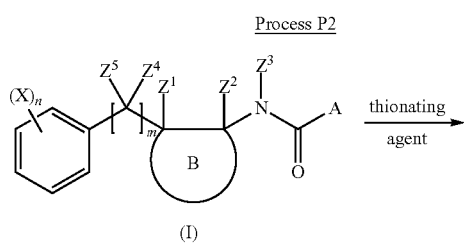

(I)

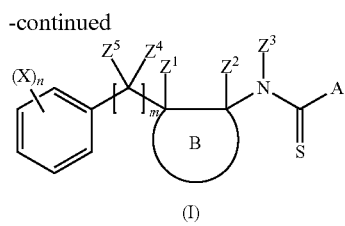

(I)

Process P2 wherein X, n, m, B, $Z^1$, $Z^2$, $Z^3$, $Z^4$, $Z^5$ and A are as herein-defined, in the optional presence of a catalytic or stoechiometric or more, quantity of a base such as an inorganic and organic base. Preference is given to using alkali metal carbonates, such as sodium carbonate, potassium carbonate, potassium bicarbonate, sodium bicarbonate; heterocyclic aromatic bases, such as pyridine, picoline, lutidine, collidine; and also tertiary amines, such as trimethylamine, triethylamine, tributylamine, N,N-dimethylaniline, N,N-dimethylaminopyridine or N-methylpiperidine.

Process P2 according to the invention is performed in the presence of a thionating agent.

Starting amide derivatives of formula (I) can be prepared according to processes P1.

Suitable thionating agents for carrying out process P2 according to the invention can be sulphur (S), sulfhydric acid ($H_2S$), sodium sulfide ($Na_2S$), sodium hydrosulfide (NaHS), boron trisulfide ($B_2S_3$), bis(diethylaluminium) sulfide (($AlEt_2$)$_2$S), ammonium sulfide (($NH_4$)$_2$S), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in *J. Chem. Soc. Perkin* 1, (2001), 358.

The compound according to the present invention can be prepared according to the general processes of preparation described above. It will nevertheless be understood that, on the basis of his general knowledge and of available publications, the skilled worker will be able to adapt this method according to the specifics of each of the compounds, which it is desired to synthesize.

Still in a further aspect, the present invention relates to compounds of formula (II) useful as intermediate compounds or materials for the process of preparation according to the invention. The present invention thus provides compounds of formula (II):

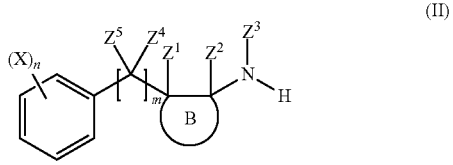

(II)

wherein X, n, m, $Z^1$, $Z^2$, $Z^3$, $Z^4$ and $Z^5$ are as herein-defined, and B represents a cyclopropyl, cyclobutyl, cyclopentyl, cyclohexyl or cycloheptyl group with the exclusion of N-cyclopropyl-2-phenylcyclohexanamine.

On the basis of the present description and his general knowledge and of available publications as for example the international patent application WO-2006/122955, the skilled person can prepare intermediate compound of formula (II) according to the present invention.

In a further aspect, the present invention also relates to a fungicide composition comprising an effective and non-phytotoxic amount of an active compound of formula (I).

The expression "effective and non-phytotoxic amount" means an amount of composition according to the invention that is sufficient to control or destroy the fungi present or liable to appear on the cropsand that does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials that are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic, organic or inorganic compound with that the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyolsand derivatives of the above compounds containing sulphate, sulphonate and phosphate functions. The presence of at least one surfactant is generally essential when the active compound and/or the inert support are water-insoluble and when the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, that complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions that are ready to be applied to the plant or seed to be treated by means of a suitable device, such as a spraying or dusting device, but also concentrated commercial compositions that must be diluted before application to the crop.

The compounds according to the invention can also be mixed with one or more insecticide, fungicide, bactericide, attractant, acaricide or pheromone active substance or other compounds with biological activity. The mixtures thus obtained have normally a broadened spectrum of activity. The mixtures with other fungicide compounds are particularly advantageous.

Examples of suitable fungicide mixing partners can be selected in the following lists:

(1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (100761-65-7), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl 1-(2,2-dimethyl-2,3-dihydro-1H-inden-1-yl)-1H-imidazole-5-carboxylate (111323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-{1-[(4-methoxyphenoxy)methyl]-2,2-dimethylpropyl} 1H-imidazole-1-carbothioate (111226-71-2).

(2) inhibitors of the respiratory chain at complex I or II, for example (2.1) bixafen (581809-46-03), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) furametpyr (123572-88-3), (2.9) furmecyclox (60568-05-0), (2.10) isopyrazam (mixture of syn-epimeric racemate 1RS,4SR,9RS and anti-epimeric racemate 1RS,4SR,9SR) (881685-58-1), (2.11) isopyrazam (anti-epimeric racemate 1RS,4SR,9SR), (2.12) isopyrazam (anti-epimeric enantiomer 1R,4S,9S), (2.13) isopyrazam (anti-epimeric enantiomer 1S,4R,9R), (2.14) isopyrazam (syn epimeric racemate 1RS,4SR,9RS), (2.15) isopyrazam (syn-epimeric enantiomer 1R,4S,9R), (2.16) isopyrazam (syn-epimeric enantiomer 1S,4R,9S), (2.17) mepronil (55814-41-0), (2.18) oxycarboxin (5259-88-1), (2.19) penflufen (494793-67-8), (2.20) penthiopyrad (183675-82-3), (2.21) sedaxane (874967-67-6), (2.22) thifluzamide (130000-40-7), (2.23) 1-methyl-N-[2-(1,1,2,2-tetrafluoroethoxy)phenyl]-3-(trifluoromethyl)-1H-pyrazole-4-carboxamide, (2.24) 3-(difluoromethyl)-1-methyl-N-(3',4',5'-trifluorobiphenyl-2-yl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide and salts thereof.

(3) inhibitors of the respiratory chain at complex III, for example (3.1) amisulbrom (348635-87-0), (3.2) azoxystrobin (131860-33-8), (3.3) cyazofamid (120116-88-3), (3.4) dimoxystrobin (141600-52-4), (3.5) enestroburin (238410-11-2) (known from WO 2004/058723), (3.6) famoxadone (131807-57-3) (known from WO 2004/058723), (3.7) fenamidone (161326-34-7) (known from WO 2004/058723), (3.8) fluoxastrobin (361377-29-9) (known from WO 2004/058723), (3.9) kresoxim-methyl (143390-89-0) (known from WO 2004/058723), (3.10) metominostrobin (133408-50-1) (known from WO 2004/058723), (3.11) orysastrobin (189892-69-1) (known from WO 2004/058723), (3.12) picoxystrobin (117428-22-5) (known from WO 2004/058723), (3.13) pyraclostrobin (175013-18-0) (known from WO 2004/058723), (3.14) pyrametostrobin (915410-70-7) (known from WO 2004/058723), (3.15) pyraoxystrobin (862588-11-2) (known from WO 2004/058723), (3.16) pyribencarb (799247-52-2) (known from WO 2004/058723), (3.17) trifloxystrobin (141517-21-7) (known from WO 2004/058723), (3.18) (2E)-2-(2-{[6-(3-chloro-2-methylphenoxy)-5-fluoropyrimidin-4-yl]oxy}phenyl)-2-(methoxyimino)-N-methylethanamide (known from WO 2004/058723), (3.19) (2E)-2-(methoxyimino)-N-methyl-2-(2-{[({(1E)-1-[3-(trifluoromethyl)phenyl]ethylidene}amino)oxy]methyl}phenyl)ethanamide (known from WO 2004/058723) and salts thereof. (3.20) (2E)-2-(methoxyimino)-N-methyl-2-{2-[(E)-({1-[3-(trifluoromethyl)phenyl]ethoxy}imino)methyl]phenyl}ethanamide (158169-73-4), (3.21) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.22) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.23) 2-chloro-N-(1,1,3-trimethyl-2,3-dihydro-1H-inden-4-yl)pyridine-3-carboxamide (119899-14-8), (3.24) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.25) methyl 2-{2-[({cyclopropyl[(4-methoxyphenyl)imino]methyl}sulfanyl)methyl]phenyl}-3-methoxyacrylate (149601-03-6), (3.26) N-(3-ethyl-3,5,5-trimethylcyclohexyl)-3-(formylamino)-2-hydroxybenzamide (226551-21-9) and salts thereof.

(4) Inhibitors of the mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5) and (4.13) 5-chloro-7-(4-methylpiperidin-1-yl)-6-(2,4,6-trifluorophenyl)[1,2,4]triazolo[1,5-a]pyrimidine (214706-53-3).

(5) Compounds capable to have a multisite action, like for example (5.1) bordeaux mixture (8011-63-0), (5.2) captafol (2425-06-1), (5.3) captan (133-06-2) (known from WO 02/12172), (5.4) chlorothalonil (1897-45-6), (5.5) copper hydroxide (20427-59-2), (5.6) copper naphthenate (1338-02-9), (5.7) copper oxide (1317-39-1), (5.8) copper oxychloride (1332-40-7), (5.9) copper (2+) sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (2234562), (5.24) maneb (12427-38-2), (5.25) metiram (9006-42-2), (5.26) metiram zinc (9006-42-2), (5.27) oxine-copper (10380-28-6), (5.28) propamidine (104-32-5), (5.29) propineb (12071-83-9), (5.30) sulphur and sulphur preparations including calcium polysulphide (7704-34-9), (5.31) thiram (137-26-8), (5.32) tolylfluanid (731-27-1), (5.33) zineb (12122-67-7), (5.34) ziram (137-30-4) and salts thereof.

(6) Compounds capable to induce a host defence, like for example (6.1) acibenzolar-S-methyl (135158-54-2), (6.2) isotianil (224049-04-1), (6.3) probenazole (27605-76-1) and (6.4) tiadinil (223580-51-6).

(7) Inhibitors of the amino acid and/or protein biosynthesis, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7) and (7.7) pyrimethanil (53112-28-0).

(8) Inhibitors of the ATP production, for example (8.1) fentin acetate (900-95-8), (8.2) fentin chloride (639-58-7), (8.3) fentin hydroxide (76-87-9), (8.4) and silthiofam (175217-20-6).

(9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of the lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1) and (11.6) tricyclazole (41814-78-2).

(12) Inhibitors of the nucleic acid synthesis, for example (12.1) benalaxyl (71626-11-4), (12.2) benalaxyl-M (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (70630-17-0), (12.11) ofurace (58810-48-3), (12.12) oxadixyl (77732-09-3) and (12.13) oxolinic acid (14698-29-4).

(13) Inhibitors of the signal transduction, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Compounds capable to act as an uncoupler, like for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds like for example (15.1) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.2) 1-[(4-methoxyphenoxy)methyl]-2,2-dimethylpropyl 1H-imidazole-1-carboxylate (111227-17-9), (15.3) 2,3,5,6-tetrachloro-4-(methylsulfonyl)pyridine (13108-52-6), (15.4) 2,3-dibutyl-6-chlorothieno[2,3-d]pyrimidin-4(3H)-one (221451-58-7), (15.5) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.6) 2-butoxy-6-iodo-3-propyl-4H-chromen-4-one, (15.7) 2-phenylphenol and salts (90-43-7), (15.8) 3,4,5-trichloropyridine-2,6-dicarbonitrile (17824-85-0), (15.9) 3-[5-(4-chlorophenyl)-2,3-dimethylisoxazolidin-3-yl]pyridine, (15.10) 3-chloro-5-(4-chlorophenyl)-4-(2,6-difluorophenyl)-6-methylpyridazine, (15.11) 4-(4-chlorophenyl)-5-(2,6-difluorophenyl)-3,6-dimethylpyridazine, (15.12) 5-amino-1,3,4-thiadiazole-2-thiol, (15.13) 5-chloro-N'-phenyl-N'-prop-2-yn-1-ylthiophene-2-sulfonohydrazide (134-31-6), (15.14) 5-methyl-6-octyl-3,7-dihydro[1,2,4]triazolo[1,5-a]pyrimidin-7-amine, (15.15) ametoctradin (865318-97-4), (15.16) benthiazole (21564-17-0), (15.17) bethoxazin (163269-30-5), (15.18) capsimycin (70694-08-5), (15.19) carvone (99-49-0), (15.20) chinomethionat (2439-01-2), (15.21) chlazafenone (688046-61-9), (15.22) cufraneb (11096-18-7), (15.23) cyflufenamid (180409-60-3), (15.24) cymoxanil (57966-95-7), (15.25) cyprosulfamide (221667-31-8), (15.26) dazomet (533-74-4), (15.27) debacarb (62732-91-6), (15.28) dichlorophen (97-23-4), (15.29) diclomezine (62865-36-5), (15.30) difenzoquat (43222-48-6), (15.31) difenzoquat methylsulphate (43222-48-6), (15.32) diphenylamine (122-39-4), (15.33) ecomate, (15.34) ethyl (2Z)-3-amino-2-cyano-3-phenylprop-2-enoate, (15.35) flumetover (154025-04-4), (15.36) fluoroimide (41205-21-4), (15.37) flusulfamide (106917-52-6), (15.38) flutianil (304900-25-2), (15.39) fosetyl-aluminium (39148-24-8), (15.40) fosetyl-calcium, (15.41) fosetyl-sodium (39148-16-8), (15.42) hexachlorobenzene (118-74-1), (15.43) irumamycin (81604-73-1), (15.44) methasulfocarb (66952-49-6), (15.45) methyl isothiocyanate (556-61-6), (15.46) metrafenone (220899-03-6), (15.47) mildiomycin (67527-71-3), (15.48) N-(4-chlorobenzyl)-3-[3-methoxy-4-(prop-2-yn-1-yloxy)phenyl]propanamide, (15.49) N-[(4-chlorophenyl)(cyano)methyl]-3-[3- methoxy-4-(prop-2-yn-1-yloxy)phenyl]propanamide, (15.50) N-[(5-bromo-3-chloropyridin-2-yl)methyl]-2,4-dichloropyridine-3-carboxamide, (15.51) N-[1-(5-bromo-3-chloropyridin-2-yl)ethyl]-2,4-dichloropyridine-3-carboxamide, (15.52) N-[1-(5-bromo-3-chloropyridin-2-yl)ethyl]-2-fluoro-4-iodopyridine-3-carboxamide, (15.53) N-{(E)-[(cyclopropylmethoxy)imino][6-(difluoromethoxy)-2,3-difluorophenyl]methyl}-2-phenylacetamide, (15.54) N-{(Z)-[(cyclopropylmethoxy)imino][6-(difluoromethoxy)-2,3-difluorophenyl]methyl}-2-phenylacetamide (221201-92-9), (15.55) natamycin (7681-93-8), (15.56) nickel dimethyldithiocarbamate (15521-65-0), (15.57) nitrothal-isopropyl (10552-74-6), (15.58) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.59) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.60) octhilinone (26530-20-1), (15.61) oxamocarb (917242-12-7), (15.62) oxyfenthiin (34407-87-9), (15.63) pentachlorophenol and salts (87-86-5), (15.64) pentyl {6-[({[(1-methyl-1H-tetrazol-5-yl)(phenyl)methylidene]amino}oxy)methyl]pyridin-2-yl} carbamate, (15.65) phenazine-1-carboxylic acid, (15.66) phenothrin, (15.67) phosphorous acid and its salts (13598-36-2), (15.68) propamocarb-fosetylate, (15.69) propanosine-sodium (88498-02-6), (15.70) proquinazid (189278-12-4), (15.71) pyrrolnitrine (1018-71-9) (known from EP-A 1 559 320), (15.72) quinolin-8-ol (134-31-6), (15.73) quinolin-8-ol sulfate (2:1) (salt) (134-31-6), (15.74) fenpyrazamine (473798-59-3), (15.75) tebufloquin (376645-78-2), (15.76) tecloftalam (76280-91-6), (15.77) tolnifanide (304911-98-6), (15.78) triazoxide (72459-58-6), (15.79) trichlamide (70193-21-4), (15.80) zarilamid (84527-51-5) and salts thereof.

The composition according to the invention comprising a mixture of a compound of formula (I) with a bactericide compound can also be particularly advantageous. Examples of suitable bactericide mixing partners can be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The compounds of formula (I) and the fungicide composition according to the invention can be used to curatively or preventively control the phytopathogenic fungi of plants or crops.

Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

Among the plants that can be protected by the method according to the invention, mention can be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rye, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots), *Elaeis* sp. (for instance oil palm); horticultural and forest crops; as well as genetically modified homologues of these crops.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, co suppression technology or RNA interference-RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 1992/005251, WO 1995/009910, WO 1998/27806, WO 2005/002324, WO 2006/021972 and U.S. Pat. No. 6,229, 072). However, genetic determinants for male sterility can also be located in the nuclear genome. Male sterile plants can also be obtained by plant biotechnology methods such as genetic engineering. A particularly useful means of obtaining male-sterile plants is described in WO 1989/10396 in which, for example, a ribonuclease such as barnase is selectively expressed in the tapetum cells in the stamens. Fertility can then be restored by expression in the tapetum cells of a ribonuclease inhibitor such as barstar (e.g. WO 1991/002069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a Petunia EPSPS (Shah et al., Science (1986), 233, 478-481), a Tomato EPSPS (Gasser et al., J. Biol. Chem. (1988), 263, 4280-4289), or an Eleusine EPSPS (WO 2001/66704). It can also be a mutated EPSPS as described in for example EP-A 0837944, WO 2000/066746, WO 2000/066747 or WO 2002/026995. Glyphosate-tolerant plants can also be obtained by expressing a gene that encodes a glyphosate oxido-reductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described in for example WO 2002/036782, WO 2003/092360, WO 2005/012515 and WO 2007/024782. Glyphosate-tolerant plants can also be obtained by selecting plants containing naturally-occurring mutations of the above-mentioned genes, as described in for example WO 2001/024615 or WO 2003/013226. Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665. Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme as described in WO 1996/038567, WO 1999/024585 and WO 1999/024586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyloxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed Science (2002), 50, 700-712, but also, in U.S. Pat. No. 5,605,011, U.S. Pat. No. 5,378,824, U.S. Pat. No. 5,141,870, and U.S. Pat. No. 5,013,659. The production of sulfonylurea-tolerant plants and imidazolinone-tolerant plants is described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and international publication WO 1996/033270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 1997/41218, for sugar beet in U.S. Pat. No. 5,773,702 and WO 1999/057965, for lettuce in U.S. Pat. No. 5,198,599, or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance. An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al., Nat. Biotechnol. (2001), 19, 668-72; Schnepf et al., Applied Environm. Microbiol. (2006), 71, 1765-1774); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose)polymerase (PARP) gene in the plant cells or plants as described in WO 2000/004173 or WO2006/045633 or PCT/EP07/004,142.
b. plants which contain a stress tolerance enhancing transgene capable of reducing the expression and/or the activity of the PARG encoding genes of the plants or plants cells, as described e.g. in WO 2004/090140.
c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g. in WO2006/032469 or WO 2006/133827 or PCT/EP07/002,433.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO99/58688, WO 1999/58690, WO 1999/58654, WO 2000/008184, WO 2000/008185, WO 2000/008175, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026, WO 1997/20936.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 1996/001904, WO 1996/021023, WO 1998/039460, and WO 1999/024593, plants producing alpha 1,4 glucans as disclosed in WO 1995/031553, US 2002/031826, U.S. Pat. No. 6,284,479, U.S. Pat. No. 5,712, 107, WO 1997/047806, WO 1997/047807, WO 1997/047808 and WO 2000/014249, plants producing alpha-1,6 branched alpha-1,4-glucans, as disclosed in WO 2000/73422, plants producing alternan, as disclosed in WO 2000/047727, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006/304779, and WO 2005/012529.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:
a) Plants, such as cotton plants, containing an altered form of cellulose synthase genes as described in WO 1998/000549
b) Plants, such as cotton plants, containing an altered form of rsw2 or rsw3 homologous nucleic acids as described in WO2004/053219
c) Plants, such as cotton plants, with increased expression of sucrose phosphate synthase as described in WO 2001/017333
d) Plants, such as cotton plants, with increased expression of sucrose synthase as described in WO02/45485
e) Plants, such as cotton plants, wherein the timing of the plasmodesmatal gating at the basis of the fiber cell is altered, e.g. through downregulation of fiberselective β 1,3-glucanase as described in WO2005/017157
f) Plants, such as cotton plants, having fibers with altered reactivity, e.g. through the expression of N-acteylglucosaminetransferase gene including nodC and chitinsynthase genes as described in WO2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:
a) Plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947
b) Plants such as oilseed rape plants, producing oil having a low linolenic acid content as described in U.S. Pat. No. 6,270,828, U.S. Pat. No. 6,169,190 or U.S. Pat. No. 5,965,755
c) Plant such as oilseed rape plants, producing oil having a low level of saturated fatty acids as described e.g. in U.S. Pat. No. 5,434,283

Particularly useful transgenic plants which may be treated according to the invention are plants which comprise one or more genes which encode one or more toxins, such as the following which are sold under the trade names YIELD GARD® (for example maize, cotton, soya beans), KnockOut® (for example maize), BiteGard® (for example maize), Bt-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or combination of transformation events, that are listed for example in the databases from various national or regional regulatory agencies (see for example http://gmoinfo.jrc.it/gmp_browse.aspx and http://www.agbios.com/dbase.php).

Among the diseases of plants or crops that can be controlled by the method according to the invention, mention can be made of:

Powdery mildew diseases such as:
  *Blumeria* diseases, caused for example by *Blumeria graminis*;
  *Podosphaera* diseases, caused for example by *Podosphaera leucotricha*;
  *Sphaerotheca* diseases, caused for example by *Sphaerotheca fuliginea*;
  *Uncinula* diseases, caused for example by *Uncinula necator*;
Rust diseases such as:
  *Gymnosporangium* diseases, caused for example by *Gymnosporangium sabinae*;
  *Hemileia* diseases, caused for example by *Hemileia vastatrix*;
  *Phakopsora* diseases, caused for example by *Phakopsora pachyrhizi* or *Phakopsora meibomiae*;
  *Puccinia* diseases, caused for example by *Puccinia recondite, Puccinia graminis* or *Puccinia striiformis*;
  *Uromyces* diseases, caused for example by *Uromyces appendiculatus*;
Oomycete diseases such as:
  *Albugo* diseases caused for example by *Albugo candida*;
  *Bremia* diseases, caused for example by *Bremia lactucae*;
  *Peronospora* diseases, caused for example by *Peronospora pisi* or *P. brassicae*;
  *Phytophthora* diseases, caused for example by *Phytophthora infestans*;
  *Plasmopara* diseases, caused for example by *Plasmopara viticola*;
  *Pseudoperonospora* diseases, caused for example by *Pseudoperonospora humuli* or *Pseudoperonospora cubensis*;
  *Pythium* diseases, caused for example by *Pythium ultimum*;
Leafspot, leaf blotch and leaf blight diseases such as:
  *Alternaria* diseases, caused for example by *Alternaria solani*;
  *Cercospora* diseases, caused for example by *Cercospora beticola*;
  *Cladiosporum* diseases, caused for example by *Cladiosporium cucumerinum*;
  *Cochliobolus* diseases, caused for example by *Cochliobolus sativus* (*Conidiaform: Drechslera*, Syn: *Helminthosporium*) or *Cochliobolus miyabeanus*;
  *Colletotrichum* diseases, caused for example by *Colletotrichum lindemuthanium*;
  *Cycloconium* diseases, caused for example by *Cycloconium oleaginum*;
  *Diaporthe* diseases, caused for example by *Diaporthe citri*;
  *Elsinoe* diseases, caused for example by *Elsinoe fawcettii*;
  *Gloeosporium* diseases, caused for example by *Gloeosporium laeticolor*;
  *Glomerella* diseases, caused for example by *Glomerella cingulata*;
  *Guignardia* diseases, caused for example by *Guignardia bidwelli*;
  *Leptosphaeria* diseases, caused for example by *Leptosphaeria maculans; Leptosphaeria nodorum*;
  *Magnaporthe* diseases, caused for example by *Magnaporthe grisea*;
  *Mycosphaerella* diseases, caused for example by *Mycosphaerella graminicola*;
*Mycosphaerella arachidicola; Mycosphaerella fijiensis*;
  *Phaeosphaeria* diseases, caused for example by *Phaeosphaeria nodorum*;
  *Pyrenophora* diseases, caused for example by *Pyrenophora teres,* or *Pyrenophora tritici repentis*;
  *Ramularia* diseases, caused for example by *Ramularia collo-cygni,* or *Ramularia areola*;
  *Rhynchosporium* diseases, caused for example by *Rhynchosporium secalis*;
  *Septoria* diseases, caused for example by *Septoria apii* or *Septoria lycopercisi*;
  *Typhula* diseases, caused for example by *Typhula incarnata*;
  *Venturia* diseases, caused for example by *Venturia inaequalis*;
Root, Sheath and stem diseases such as:
  *Corticium* diseases, caused for example by *Corticium graminearum*;
  *Fusarium* diseases, caused for example by *Fusarium oxysporum*;
  *Gaeumannomyces* diseases, caused for example by *Gaeumannomyces graminis*;
  *Rhizoctonia* diseases, caused for example by *Rhizoctonia solani*;
  *Sarocladium* diseases caused for example by *Sarocladium oryzae*;
  *Sclerotium* diseases caused for example by *Sclerotium oryzae*;
  *Tapesia* diseases, caused for example by *Tapesia acuformis*;
  *Thielaviopsis* diseases, caused for example by *Thielaviopsis basicola*;
Ear and panicle diseases such as:
  *Alternaria* diseases, caused for example by *Alternaria* spp.;
  *Aspergillus* diseases, caused for example by *Aspergillus flavus*;
  *Cladosporium* diseases, caused for example by *Cladosporium* spp.;
  *Claviceps* diseases, caused for example by *Claviceps purpurea*;
  *Fusarium* diseases, caused for example by *Fusarium culmorum*;
  *Gibberella* diseases, caused for example by *Gibberella zeae*;
  *Monographella* diseases, caused for example by *Monographella nivalis*;
Smut and bunt diseases such as:
  *Sphacelotheca* diseases, caused for example by *Sphacelotheca reiliana*;
  *Tilletia* diseases, caused for example by *Tilletia caries*;
  *Urocystis* diseases, caused for example by *Urocystis occulta*;
  *Ustilago* diseases, caused for example by *Ustilago nuda*;

Fruit rot and mould diseases such as:
  Aspergillus diseases, caused for example by *Aspergillus flavus*;
  Botrytis diseases, caused for example by *Botrytis cinerea*;
  Penicillium diseases, caused for example by *Penicillium expansum*;
  Rhizopus diseases caused by example by *Rhizopus stolonifer*
  Sclerotinia diseases, caused for example by *Sclerotinia sclerotiorum*;
  Verticilium diseases, caused for example by *Verticilium alboatrum*;
Seed and soilborne decay, mould, wilt, rot and damping-off diseases:
  Alternaria diseases, caused for example by *Alternaria brassicicola*
  Aphanomyces diseases, caused for example by *Aphanomyces euteiches*
  Ascochyta diseases, caused for example by *Ascochyta lentis*
  Aspergillus diseases, caused for example by *Aspergillus flavus*
  Cladosporium diseases, caused for example by *Cladosporium herbarum*
  Cochliobolus diseases, caused for example by *Cochliobolus sativus*
  (Conidiaform: *Drechslera*, *Bipolaris* Syn: *Helminthosporium*);
  Colletotrichum diseases, caused for example by *Colletotrichum coccodes*;
  Fusarium diseases, caused for example by *Fusarium culmorum*;
  Gibberella diseases, caused for example by *Gibberella zeae*;
  Macrophomina diseases, caused for example by *Macrophomina phaseolina*
  Monographella diseases, caused for example by *Monographella nivalis*;
  Penicillium diseases, caused for example by *Penicillium expansum*
  Phoma diseases, caused for example by *Phoma lingam*
  Phomopsis diseases, caused for example by *Phomopsis sojae*;
  Phytophthora diseases, caused for example by *Phytophthora cactorum*;
  Pyrenophora diseases, caused for example by *Pyrenophora graminea*
  Pyricularia diseases, caused for example by *Pyricularia oryzae*;
  Pythium diseases, caused for example by *Pythium ultimum*;
  Rhizoctonia diseases, caused for example by *Rhizoctonia solani*;
  Rhizopus diseases, caused for example by *Rhizopus oryzae*
  Sclerotium diseases, caused for example by *Sclerotium rolfsii*;
  Septoria diseases, caused for example by *Septoria nodorum*;
  Typhula diseases, caused for example by *Typhula incarnata*;
  Verticillium diseases, caused for example by *Verticillium dahliae*;
Canker, broom and dieback diseases such as:
  Nectria diseases, caused for example by *Nectria galligena*;
Blight diseases such as:
  Monilinia diseases, caused for example by *Monilinia laxa*;
Leaf blister or leaf curl diseases such as:
  Exobasidium diseases caused for example by *Exobasidium vexans*
  Taphrina diseases, caused for example by *Taphrina deformans*;
Decline diseases of wooden plants such as:
  Esca diseases, caused for example by *Phaemoniella clamydospora*;
  Eutypa dyeback, caused for example by *Eutypa lata*;
  Ganoderma diseases caused for example by *Ganoderma boninense*;
  Rigidoporus diseases caused for example by *Rigidoporus lignosus*
Diseases of Flowers and Seeds such as
  Botrytis diseases caused for example by *Botrytis cinerea*;
Diseases of Tubers such as
  Rhizoctonia diseases caused for example by *Rhizoctonia solani*;
  Helminthosporium diseases caused for example by *Helminthosporium solani*;
Club root diseases such as
  Plasmodiophora diseases, cause for example by *Plamodiophora brassicae*.
Diseases caused by Bacterial Organisms such as
  Xanthomonas species for example *Xanthomonas campestris* pv. *oryzae*;
  Pseudomonas species for example *Pseudomonas syringae* pv. *lachrymans*;
  Erwinia species for example *Erwinia amylovora*.

The composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The compounds or mixtures according to the invention can also be used for the preparation of composition useful to curatively or preventively treat human or animal fungal diseases such as, for example, mycoses, dermatoses, *trichophyton* diseases and candidiases or diseases caused by *Aspergillus* spp., for example *Aspergillus fumigatus*.

The various aspects of the invention will now be illustrated with reference to the following table of compound examples and the following preparation or efficacy examples.

Table 1 illustrates in a non-limiting manner examples of compounds of formula (I) according to the invention.

In table 1, M+H (ApcI+) means the molecular ion peak plus 1 a.m.u. (atomic mass unit) as observed in mass spectroscopy via positive atmospheric pressure chemical ionisation.

TABLE 1

| Example | A | T | Z1 | Z2 | Z3 | m | Z4 | Z5 | B | (X)n-phenyl | Mass (M + H) |
|---|---|---|---|---|---|---|---|---|---|---|---|
| 1 | 3-ethyl-5-fluoro-1-methyl-pyrazol-4-yl | O | H | H | cPr | 0 | | | cyclopentyl | 2-chlorophenyl | 390 |
| 2 | 3-(difluoromethyl)-1-methyl-pyrazol-4-yl | O | H | H | cPr | 0 | | | cyclopentyl | 2-chlorophenyl | 394 |
| 3 | 5-fluoro-1,3-dimethyl-pyrazol-4-yl | O | H | H | cPr | 0 | | | cyclopentyl | 2-chlorophenyl | 376 |
| 4 | 4-(difluoromethyl)-2-methyl-thiazol-5-yl | O | H | H | cPr | 0 | | | cyclopentyl | 2-chlorophenyl | 411 |
| 5 | 2,5-dimethyl-furan-3-yl | O | H | H | cPr | 0 | | | cyclopentyl | 2-chlorophenyl | 358 |
| 6 | 3-ethyl-5-fluoro-1-methyl-pyrazol-4-yl | O | H | H | cPr | 0 | | | cyclopentyl | 2,4-dichlorophenyl | 424 |
| 7 | 3-(difluoromethyl)-1-methyl-pyrazol-4-yl | O | H | H | cPr | 0 | | | cyclopentyl | 2,4-dichlorophenyl | 428 |
| 8 | 5-fluoro-1,3-dimethyl-pyrazol-4-yl | O | H | H | cPr | 0 | | | cyclopentyl | 2,4-dichlorophenyl | 410 |
| 9 | 4-(difluoromethyl)-2-methyl-thiazol-5-yl | O | H | H | cPr | 0 | | | cyclopentyl | 2,4-dichlorophenyl | 445 |

TABLE 1-continued

| Example | A | T | Z1 | Z2 | Z3 | m | Z4 | Z5 | B | (X)n-phenyl | Mass (M + H) |
|---|---|---|---|---|---|---|---|---|---|---|---|
| 10 | 2,5-dimethylfuran-3-yl | O | H | H | cPr | 0 | | | cyclopentyl | 2,4-dichlorophenyl | 392 |
| 11 | 1,3,5-trimethylpyrazol-4-yl | O | H | H | cPr | 0 | | | trans-cyclohexyl | phenyl | 352 |
| 12 | 3-iodo-1-methylpyrazol-4-yl | O | H | H | cPr | 0 | | | trans-cyclohexyl | phenyl | 450 |
| 13 | 3-ethyl-5-fluoro-1-methylpyrazol-4-yl | O | H | H | cPr | 0 | | | trans-cyclohexyl | phenyl | 370 |
| 14 | 3-ethyl-5-fluoro-1-methylpyrazol-4-yl | O | H | H | cPr | 1 | H | H | cyclohexyl | phenyl | 384 |
| 15 | 3-(difluoromethyl)-1-methylpyrazol-4-yl | O | H | H | cPr | 0 | | | cis-cyclohexyl | phenyl | 374 |
| 16 | 3-(difluoromethyl)-1-methylpyrazol-4-yl | O | H | H | cPr | 1 | H | H | cyclohexyl | phenyl | 388 |
| 17 | 3-(difluoromethyl)-1-methylpyrazol-4-yl | O | H | H | cPr | 0 | | | trans-cyclohexyl | phenyl | 374 |
| 18 | 5-fluoro-1,3-dimethylpyrazol-4-yl | O | H | H | cPr | 0 | | | cis-cyclohexyl | phenyl | 356 |

TABLE 1-continued

| Example | A | T | Z1 | Z2 | Z3 | m | Z4 | Z5 | B | (X)n-phenyl | Mass (M + H) |
|---|---|---|---|---|---|---|---|---|---|---|---|
| 19 | 3-methyl-1-methyl-5-fluoro-pyrazol-4-yl | O | H | H | cPr | 1 | H | H | cyclohexyl | phenyl | 370 |
| 20 | 3-methyl-1-methyl-5-fluoro-pyrazol-4-yl | S | H | H | cPr | 0 | | | cis-cyclohexyl | phenyl | 372 |
| 21 | 4-trifluoromethyl-1-methyl-pyrrol-3-yl | O | H | H | cPr | 0 | | | trans-cyclohexyl | phenyl | 391 |
| 22 | 4-trifluoromethyl-1-methyl-pyrrol-3-yl | S | H | H | cPr | 0 | | | trans-cyclohexyl | phenyl | 407 |
| 23 | 4-difluoromethyl-2-methyl-thiazol-5-yl | O | H | H | cPr | 0 | | | trans-cyclohexyl | phenyl | 391 |
| 24 | 4-trifluoromethyl-2-methyl-thiazol-5-yl | O | H | H | cPr | 0 | | | trans-cyclohexyl | phenyl | 409 |
| 25 | 3-trifluoromethyl-1-methyl-pyrazol-4-yl | O | H | H | cPr | 0 | | | trans-cyclohexyl | phenyl | 392 |
| 26 | 3-ethyl-1-methyl-5-fluoro-pyrazol-4-yl | O | H | H | cPr | 0 | | | cyclohexyl | 2-chlorophenyl | 404 |

TABLE 1-continued

| Example | A | T | Z1 | Z2 | Z3 | m | Z4 | Z5 | B | (X)n phenyl | Mass (M + H) |
|---|---|---|---|---|---|---|---|---|---|---|---|
| 27 | 3-(difluoromethyl)-1-methyl-pyrazol-4-yl | O | H | H | cPr | 0 | | | cyclohexyl | 2-chlorophenyl | 408 |
| 28 | 5-fluoro-1,3-dimethyl-pyrazol-4-yl | O | H | H | cPr | 0 | | | cyclohexyl | 2-chlorophenyl | 390 |
| 29 | 4-(difluoromethyl)-2-methyl-thiazol-5-yl | O | H | H | cPr | 0 | | | cyclohexyl | 2-chlorophenyl | 425 |
| 30 | 2,5-dimethylfuran-3-yl | O | H | H | cPr | 0 | | | cyclohexyl | 2-chlorophenyl | 372 |
| 31 | 3-ethyl-5-fluoro-1-methyl-pyrazol-4-yl | O | H | H | cPr | 0 | | | cyclohexyl | 2,4-dichlorophenyl | 438 |
| 32 | 3-(difluoromethyl)-1-methyl-pyrazol-4-yl | O | H | H | cPr | 0 | | | cyclohexyl | 2,4-dichlorophenyl | 442 |
| 33 | 5-fluoro-1,3-dimethyl-pyrazol-4-yl | O | H | H | cPr | 0 | | | cyclohexyl | 2,4-dichlorophenyl | 424 |
| 34 | 4-(difluoromethyl)-2-methyl-thiazol-5-yl | O | H | H | cPr | 0 | | | cyclohexyl | 2,4-dichlorophenyl | 459 |
| 35 | 2,5-dimethylfuran-3-yl | O | H | H | cPr | 0 | | | cyclohexyl | 2,4-dichlorophenyl | 406 |

The following examples illustrate in a non-limiting manner the preparation and efficacy of the compounds of formula (I) according to the invention.

PREPARATION EXAMPLE 1

Preparation of cis-N-cyclopropyl-5-fluoro-1,3-dimethyl-N-(2-phenyl cyclohexyl)-1H-pyrazole-4-carboxamide (compound 18)

Step 1: preparation of cis and trans-N-cyclopropyl-2-phenyl-cyclohexanamine

To a cooled solution of 2.78 ml (40 mmol) of cyclopropylamine and 2.87 ml (50 mmol) of acetic acid, together with 5 g of 3 Å molecular sieves, in 50 ml of methanol, are added 3.5 g (20 mmol) of 2-phenylcyclohexanone. The reaction mixture is stirred for 3.5 hrs at reflux. The reaction mixture is then cooled to 0° C. and 3 g (50 mmol) of sodium cyanoborohydride are slowly added and the reaction mixture is further stirred for 2 hrs at reflux. The cooled reaction mixture is then filtered over a cake of diatomaceous earth. The cake is washed twice by 80 ml of methanol and the combined methanolic extracts are concentrated under vacuum. 100 ml of water are then added to the residue and the pH is ajusted to 12 with a 1 N solution of sodium hydroxyde. The watery layer is extracted with 100 ml of ethyl acetate. The organic layer is washed twice by brine and dried over magnesium sulfate to yield after concentration 3.52 g of a yellow oil. Column chromatography on silica gel (gradient heptane/ethyl acetate) yields 1.0 g (23% yield) of cis-N-cyclopropyl-2-phenylcyclohexanamine as a yellow oil (M+H=216) and 1.9 g (44% yield) of trans-N-cyclopropyl-2-phenylcyclohexanamine as a colorless oil (M+H=216).

Step 2: preparation of cis-N-cyclopropyl-5-fluoro-1,3-dimethyl-N-(2-phenylcyclo hexyl)-1H-pyrazole-4-carboxamide At ambient temperature, a solution of 180 mg (1.02 mmol) of 5-fluoro-1,3-dimethyl-1H-pyrazole-4-carbonyl chloride in 1 ml of tetrahydrofurane is added dropwise to a solution of 200 mg (0.93 mmol) of cis-N-cyclopropyl-2-phenylcyclohexanamine and 100 mg (1.02 mmol) of triethylamine in 5 ml of tetrahydrofurane. The reaction mixture is stirred for 2 hrs at 70° C. The solvent is removed under vacuum and 100 ml of water are then added to the residue. The watery layer is extracted twice with ethyl acetate (2×50 ml) and the combined organic layers are successively washed by a 1 N solution of HCl, a saturated solution of potassium carbonate and brine and dried over a Chemelut™ cartridge to yield after concentration 380 mg of a yellow oil. Column chromatography on silica gel (gradient heptane/ethyl acetate) yields 160 mg (46% yield) of cis-N-cyclopropyl-5-fluoro-1,3-dimethyl-N-(2-phenylcyclohexyl)-1H-pyrazole-4-carboxamide as a colorless oil (M+H=356).

GENERAL PREPARATION EXAMPLE

Thionation of Amide of Formula (I) on Chemspeed Apparatus

In a 13 ml Chemspeed vial is weighted 0.27 mmole of phosphorous pentasulfide ($P_2S_5$). 3 ml of a 0.18 molar solution of the amide (I) (0.54 mmole) in dioxane is added and the mixture is heated at reflux for two hours. The temperature is then cooled to 80° C. and 2.5 ml of water are added. The mixture is heated at 80° C. for one more hour. 2 ml of water are then added and the reaction mixture is extracted twice by 4 ml of dichloromethane. The organic phase is deposited on a basic alumina cardridge (2 g) and eluted twice by 8 ml of dichloromethane. The solvents are removed and the crude thioamide derivative is analyzed by LCMS and NMR. Insufficiently pure compounds are further purified by preparative LCMS.

Example A

In Vivo Test on *Puccinia recondita* (Brown Rust)

The active ingredients tested are prepared by homogenization in a mixture of acetone/tween/DMSO, then diluted with water to obtain the desired active material.

Wheat plants (Scipion variety) sown on 50/50 peat soil-pozzolana substrate in starter cups and grown at 12° C., are treated at the 1-leaf stage (10 cm tall) by spraying with the aqueous suspension described above.

Plants, used as controls, are treated with an aqueous solution not containing the active material. After 24 hours, the plants are contaminated by spraying the leaves with an aqueous suspension of *Puccinia recondita* spores (100,000 spores per ml). The spores are collected from a 10-day-old contaminated wheat and are suspended in water containing 2.5 ml/l of tween 80 10%. The contaminated wheat plants are incubated for 24 hours at 20° C. and at 100% relative humidity, and then for 10 days at 20° C. and at 70% relative humidity.

Grading is carried out 10 days after the contamination, in comparison with the control plants. Under these conditions, good (at least 70%) or total protection is observed at a dose of 500 ppm with the following compounds: 13, 17 and 18.

Example B

In Vivo Test on *Mycosphaerella graininicola* (Wheat Leaf Spot)

The active ingredients tested are prepared by homogenization in a mixture of acetone/tween/DMSO, then diluted with water to obtain the desired active material concentration.

Wheat plants (Scipion variety), sown on a 50/50 peat soil-pozzolana substrate in starter cups and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Mycosphaerella graminicola* spores (500 000 spores per ml). The spores are collected from a 7-day-old culture. The contaminated wheat plants are incubated for 72 hours at 18° C. and at 100% relative humidity, and then for 21 to 28 days at 90% relative humidity. Grading (% of efficacy) is carried out 21 to 28 days after the contamination, in comparison with the control plants.

Under these conditions, good (at least 70%) or total protection is observed at a dose of 500 ppm with the following compounds: 13, 15, 17, 18, 21 and 25.

Example C

In Vivo Test on *Alternaria Brassicae* (Leaf Spot of Crucifers)

The active ingredients tested are prepared by homogenization in a mixture of acetone/tween/DMSO, and then diluted with water to obtain the desired active material.

Radish plants (Pernot variety), sown on a 50/50 peat soil-pozzolana substrate in starter cups and grown at 18-20° C., are treated at the cotyledon stage by spraying with the active ingredient prepared as described above.

Plants, used as controls, are treated with the mixture of acetone/tween/water not containing the active material.

After 24 hours, the plants are contaminated by spraying them with an aqueous suspension of *Alternaria brassicae* spores (40,000 spores per cm3). The spores are collected from a 12 to 13 days-old culture.

The contaminated radish plants are incubated for 6-7 days at about 18° C., under a humid atmosphere.

Grading is carried out 6 to 7 days after the contamination, in comparison with the control plants. Under these conditions, good protection (at least 70%) is observed at a dose of 500 ppm with the following compounds: 12, 13, 15, 17, 21, 23 and 25.

Example D

In Vivo Test on *Sphaerotheca fuliginea* (Cucurbits Powdery Mildew)

The active ingredients tested are prepared by homogenization in a mixture of acetone/tween/DMSO, then diluted with water to obtain the desired active material.

Gherkin plants (Vert petit de Paris variety) in starter cups, sown on a 50/50 peat soil-pozzolana substrate and grown at 20° C./23° C., are treated at the cotyledon Z10 stage by spraying with the aqueous suspension described above. Plants, used as controls, are treated with an aqueous solution not containing the active material.

After 24 hours, the plants are contaminated by spraying them with an aqueous suspension of *Sphaerotheca fuliginea* spores (100 000 spores per ml). The spores are collected from a contaminated plants. The contaminated gherkin plants are incubated at about 20° C./25° C. and at 60/70% relative humidity.

Grading (% of efficacy) is carried out 12 days after the contamination, in comparison with the control plants.

Under these conditions, good (at least 70%) or total protection is observed at a dose of 500 ppm with the following compounds: 12, 13, 17, 18, 21 and 25.

Example E

In Vivo Test on *Pyrenophora teres* (Barley)/Preventive

Solvent: 49 parts by weight of N,N-dimethylformamide
Emulsifier: 1 part by weight of Alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Pyrenophora teres*. The plants remain for 48 hours in an incubation cabinet at 22° C. and a relative atmospheric humidity of 100%. Then the plants are placed in a greenhouse at a temperature of approximately 20° C. and a relative atmospheric humidity of approximately 80%.

The test is evaluated 7-9 days after the inoculation. 0% means an efficacy which corresponds to that of the control while an efficacy of 100% means that no disease is observed.

In this test the compounds according to the invention of the following structures showed efficacy of 70% or even higher at a concentration of 500 ppm of active ingredient: 1, 2, 3, 4, 5, 6, 7, 8, 9, 10, 14, 16, 20, 27, 28, 32 and 33.

Example F

In Vivo Test on *Venturia inaequalis* (Apple Scab)/Protective

Solvent: 24.5 parts by weight of acetone
24.5 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous conidia suspension of the causal agent of apple scab (*Venturia inaequalis*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the control, while an efficacy of 100% means that no disease is observed. In this test the following compounds according to the invention showed efficacy of 70% or even higher at a concentration of 100 ppm of active ingredient: 14 and 19.

Example G

In Vivo Test on *Septoria tritici* (Wheat)/Preventive

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has dried on, the plants are sprayed with a spore suspension of *Septoria tritici*. The plants remain for 48 hours in an incubation cabinet at approximately 20° C. and a relative atmospheric humidity of approximately 100% and then 60 hours at approximately 15° C. in a translucent incubation cabinet at a relative atmospheric humidity of approximately 100%.

The plants are placed in a greenhouse at a temperature of approximately 15° C. and a relative atmospheric humidity of approximately 80%.

The test is evaluated 21 days after the inoculation. 0% means an efficacy which corresponds to that of the control, while an efficacy of 100% means that no disease is observed.

In this test the following. compounds according to the invention showed an efficacy of 70% or even higher at a concentration of 500 ppm of active ingredient 14, 16 and 19.

Example H

In Vivo Comparative Test on *Leptosphaeria nodoruin* (Wheat)/Preventive

Solvent: 49 parts by weight of N,N-dimethylacetamide
Emulsifier: 1 part by weight of alkylaryl polyglycol ether To produce a suitable preparation of active compound, 1 part by weight of active compound or the compound combination is mixed with the stated amounts of solvent and emulsifier, and the concentrate is diluted with water to the desired concentration.

To test for protective activity, young plants are sprayed with a preparation of active compound or active compound combination at the stated rate of application. After the spray coating has dried on, the plants are sprayed with a spore suspension of *Leptosphaeria nodosum*. The plants remain for 48 hours in an incubation cabinet at 20° C. and a relative atmospheric humidity of 100%.

The plants are placed in a greenhouse at a temperature of approximately 15° C. and a relative atmospheric humidity of approximately 80%.

The test is evaluated 10 days after the inoculation. 0% means an efficacy which corresponds to that of the control, while an efficacy of 100% means that no disease is observed.

Under these conditions, good (at least 70% of disease control or higher) is observed at a dose of 500 ppm with the following compounds: 7 and 32 according to the invention whereas weak protection (less than 10% of disease control) is observed at a dose of 500 ppm with the compounds of example 1.001 disclosed in international patent application WO-2007/134799. Example 1.001 disclosed in patent application WO-2007/134799 corresponds to the following compound: cis-N-[2-(4-chlorophenyl)cyclopropyl]-3-(difluoromethyl)-1-methyl-1H-pyrazole-4-carboxamide These results show that the compounds according to the invention have a much better biological activity than the structurally closest compound disclosed in WO-2007/134799.

The invention claimed is:

1. A compound of formula (I)

(I)

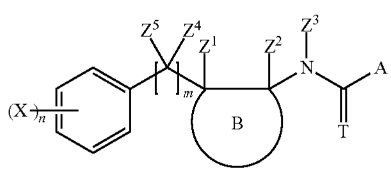

wherein

A is a carbo-linked, unsaturated or partially saturated, 5-membered heterocyclyl group that can be substituted by up to four groups R;

T is O or S;

B is a 3-, 4-, 5-, 6- or 7-membered non aromatic carbocycle that can be substituted by up to four $C_1$-$C_8$-alkyl groups;

n is 0, 1, 2, 3, 4 or 5;

m is 0 or 1;

each X is independently selected from the group consisting of a halogen atom; nitro; cyano; isonitrile; hydroxy; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-halogenoalkyl having 1 to 5 halogen atoms; substituted or non-substituted $C_2$-$C_8$-alkenyl; $C_2$-$C_8$-halogenoalkenyl having 1 to 5 halogen atoms; substituted or non-substituted $C_2$-$C_8$-alkynyl; $C_2$-$C_8$-halogenoalkynyl having 1 to 5 halogen atoms; substituted or non-substituted $C_1$-$C_8$-alkoxy; $C_1$-$C_8$-halogenoalkoxy having 1 to 5 halogen atoms; substituted or non-substituted $C_1$-$C_8$-alkylsulfanyl; $C_1$-$C_8$-halogenoalkylsulfanyl having 1 to 5 halogen atoms; substituted or non-substituted $C_1$-$C_8$-alkylsulfinyl; $C_1$-$C_8$-halogenoalkylsulfinyl having 1 to 5 halogen atoms; substituted or non-substituted $C_1$-$C_8$-alkylsulfonyl; $C_1$-$C_8$-halogenoalkylsulfonyl having 1 to 5 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-halogenoalkenyloxy having 1 to 5 halogen atoms; substituted or non-substituted $C_3$-$C_8$-alkynyloxy; $C_2$-$C_8$-halogenoalkynyloxy having 1 to 5 halogen atoms; substituted or non-substituted $C_3$-$C_7$-cycloalkyl; $C_3$-$C_7$-halogenocycloalkyl having 1 to 5 halogen atoms; substituted or non-substituted ($C_3$-$C_7$-cycloalkyl)-$C_1$-$C_8$-alkyl; substituted or non-substituted ($C_3$-$C_7$-cycloalkyl)-$C_2$-$C_8$-alkenyl; substituted or non-substituted ($C_3$-$C_7$-cycloalkyl)-$C_2$-$C_8$-alkynyl; substituted or non-substituted tri $C_1$-$C_8$ alkylsilyl; substituted or non-substituted tri($C_1$-$C_8$)alkylsilyl-$C_1$-$C_8$-alkyl; substituted or non-substituted $C_1$-$C_8$-alkylcarbonyl; $C_1$-$C_8$-halogenoalkylcarbonyl having 1 to 5 halogen atoms; substituted or non-substituted $C_1$-$C_8$-alkylcarbonyloxy; $C_1$-$C_8$-halogenoalkylcarbonyloxy having 1 to 5 halogen atoms; substituted or non-substituted $C_1$-$C_8$-alkylcarbonylamino; $C_1$-$C_8$-halogenoalkyl-carbonylamino having 1 to 5 halogen atoms; substituted or non-substituted $C_1$-$C_8$-alkoxycarbonyl; $C_1$-$C_8$-halogenoalkoxycarbonyl having 1 to 5 halogen atoms; substituted or non-substituted $C_1$-$C_8$-alkyloxycarbonyloxy; $C_1$-$C_8$-halogenoalkoxycarbonyloxy having 1 to 5 halogen atoms; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl that can be substituted by up to 6 groups Q; $C_1$-$C_8$-arylalkyl that can be substituted by up to 6 groups Q; $C_2$-$C_8$-arylalkenyl that can be substituted by up to 6 groups Q; $C_2$-$C_8$-arylalkynyl that can be substituted by up to 6 groups Q; aryloxy that can be substituted by up to 6 groups Q; arylsulfanyl that can be substituted by up to 6 groups Q; arylamino that can be substituted by up to 6 groups Q; $C_1$-$C_8$-arylalkyloxy that can be substituted by up to 6 groups Q; $C_1$-$C_8$-arylalkylsulfanyl that can be substituted by up to 6 groups Q; and $C_1$-$C_8$-arylalkylamino that can be substituted by up to 6 groups Q; or two substituents X together with the consecutive carbon atoms to which they are linked can form a 5- or 6-membered, saturated carbocycle or 5- or 6-membered, saturated heterocycle, which can be substituted by up to four groups Q which can be the same or different;

$Z^1$ and $Z^2$ are independently selected from the group consisting of a hydrogen atom; a halogen atom; cyano; a substituted or non-substituted $C_1$-$C_8$-alkyl; $C_1$-$C_8$-halogenoalkyl having 1 to 5 halogen atoms; substituted or non-substituted $C_1$-$C_8$-alkoxy; substituted or non-substituted $C_1$-$C_8$-alkylsulfanyl; and substituted or non-substituted $C_1$-$C_8$-alkoxycarbonyl;

$Z^3$ is a non-substituted $C_3$-$C_7$-cycloalkyl or a $C_3$-$C_7$-cycloalkyl substituted by up to 10 substituents independently selected from the group consisting of halogen atoms, cyano, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl and di-$C_1$-$C_8$-alkylamino-carbonyl;

$Z^4$ and $Z^5$ are independently selected from the group consisting of a hydrogen atom; a halogen atom; cyano; a substituted or non-substituted $C_1$-$C_8$-alkyl; $C_1$-$C_8$-halogenoalkyl having 1 to 5 halogen atoms; substituted or non-substituted $C_1$-$C_8$-alkoxy; substituted or non-substituted $C_1$-$C_8$-alkylsulfanyl; substituted or non-substituted $C_1$-$C_8$-alkoxycarbonyl; or $Z^4$ and $Z^5$ comprise a $C_2$-$C_5$-alkylene group that can be substituted by up to four $C_1$-$C_8$-alkyl groups;

each Q is independently selected from the group consisting of a halogen atom; cyano; nitro; substituted or non-substituted $C_1$-$C_8$-alkyl; $C_1$-$C_8$-halogenoalkyl having 1 to 9 halogen atoms that can be the same or different; substituted or non-substituted $C_1$-$C_8$-alkoxy; $C_1$-$C_8$-halogenoalkoxy having 1 to 9 halogen atoms that can be the same or different; substituted or non-substituted $C_1$-$C_8$-alkylsulfanyl; $C_1$-$C_8$-halogenoalkylsulfanyl having 1 to 9 halogen atoms that can be the same or different; substituted or non-substituted tri($C_1$-$C_8$)alkylsilyl; substituted or non-substituted tri($C_1$-$C_8$)alkylsilyl-$C_1$-$C_8$-alkyl; substituted or non-substituted ($C_1$-$C_8$-alkoxyimino)-$C_1$-$C_8$-alkyl; and substituted or non-substituted (benzyloxyimino)-$C_1$-$C_8$-alkyl;

each R is independently selected from the group consisting of hydrogen atom; halogen atom; nitro; cyano; hydroxy; amino; sulfanyl; pentafluoro-$\lambda^6$-sulfanyl; substituted or non-substituted ($C_1$-$C_8$-alkoxyimino)-$C_1$-$C_8$-alkyl; substituted or non-substituted (benzyloxyimino)-$C_1$-$C_8$-alkyl; substituted or non-substituted $C_1$-$C_8$-alkyl; $C_1$-$C_8$-halogenoalkyl having 1 to 5 halogen atoms; substituted or non-substituted $C_2$-$C_8$-alkenyl; $C_2$-$C_8$-halogenoalkenyl having 1 to 5 halogen atoms; substituted or non-substituted $C_2$-$C_8$-alkynyl; $C_2$-$C_8$-halogenoalkynyl having 1 to 5 halogen atoms; substituted or non-substituted $C_1$-$C_8$-alkoxy; $C_1$-$C_8$-halogenoalkoxy having 1 to 5 halogen atoms; substituted or non-substituted $C_1$-$C_8$-alkylsulfanyl; $C_1$-$C_8$-halogenoalkylsulfanyl having 1 to 5 halogen atoms; substituted or non-substituted $C_1$-$C_8$-alkylsulfinyl; $C_1$-$C_8$-halogenoalkylsulfinyl having 1 to 5 halogen atoms; substituted or non-substituted $C_1$-$C_8$-alkylsulfonyl; $C_1$-$C_8$-halogenoalkylsulfonyl having 1 to 5 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; substituted or non-substituted $C_3$-$C_8$-alkynyloxy; substituted or non-substituted $C_3$-$C_7$-cycloalkyl; $C_3$-$C_7$-halogenocycloalkyl having 1 to 5 halogen atoms; substituted or non-substituted tri($C_1$-$C_8$)alkylsilyl; substituted or non-substituted $C_1$-$C_8$-alkylcarbonyl; $C_1$-$C_8$-halogenoalkylcarbonyl having 1 to 5 halogen atoms; substituted or non-substituted $C_1$-$C_8$-alkoxycarbonyl; $C_1$-$C_8$ halogenoalkoxycarbonyl having 1 to 5 halogen atoms; substituted or non-substituted $C_1$-$C_8$-alkylcarbamoyl; substituted or non-substituted di-$C_1$-$C_8$-alkylcarbamoyl; phenoxy; phenylsulfanyl; phenylamino; benzyloxy; benzylsulfanyl; ear and benzylamino;

as well as any salt, N-oxide, or optically active isomer thereof.

2. The compound of claim 1 wherein A is selected from the group consisting of:

a heterocycle of formula ($A^1$)

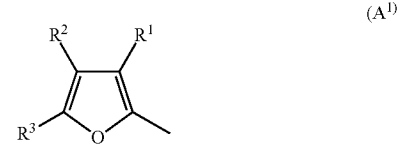

wherein:
$R^1$, $R^2$, and $R^3$ are independently selected from the group consisting of a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy, and $C_1$-$C_5$-halogenoalkoxy comprising up to 9 halogen atoms that can be the same or different;

a heterocycle of formula ($A^2$)

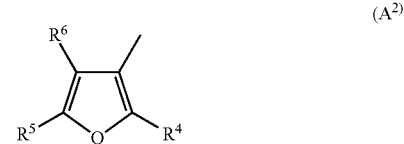

wherein:
$R^4$, $R^5$, and $R^6$ are independently selected from the group consisting of a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy, and $C_1$-$C_5$-halogenoalkoxy comprising up to 9 halogen atoms that can be the same or different;

a heterocycle of formula ($A^3$)

wherein:
$R^7$ is selected from the group consisting of a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy, and $C_1$-$C_5$-halogenoalkoxy comprising up to 9 halogen atoms that can be the same or different;

$R^8$ is selected from the group consisting of a hydrogen atom and a substituted or non-substituted $C_1$-$C_5$-alkyl;

a heterocycle of formula (A⁴)

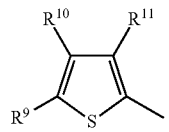
(A⁴)

wherein:
R⁹, R¹⁰, and R¹¹ are independently selected from the group consisting of a hydrogen atom; a halogen atom; substituted or non-substituted $C_1$-$C_5$-alkyl; amino; substituted or non-substituted $C_1$-$C_5$-alkoxy; substituted or non-substituted $C_1$-$C_5$-alkylsulfanyl; $C_1$-$C_5$-halogenoalkyl comprising up to 9 halogen atoms that can be the same or different and $C_1$-$C_5$-halogenoalkoxy comprising up to 9 halogen atoms that can be the same or different;

a heterocycle of formula (A⁵)

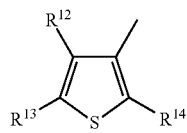
(A⁵)

wherein:
R¹² and R¹³ are independently selected from the group consisting of a hydrogen atom; a halogen atom; substituted or non-substituted $C_1$-$C_5$-alkyl; substituted or non-substituted $C_1$-$C_5$-alkoxy; amino; $C_1$-$C_5$-halogenoalkyl comprising up to 9 halogen atoms that can be the same or different and $C_1$-$C_5$-halogenoalkoxy comprising up to 9 halogen atoms that can be the same or different;
R¹⁴ is selected from the group consisting of a hydrogen atom; a halogen atom; substituted or non-substituted $C_1$-$C_5$-alkyl; substituted or non-substituted $C_1$-$C_5$-alkoxy; amino; $C_1$-$C_5$-halogenoalkyl comprising up to 9 halogen atoms that can be the same or different and $C_1$-$C_5$-halogenoalkoxy comprising up to 9 halogen atoms that can be the same or different; a heterocycle of formula (A⁶)

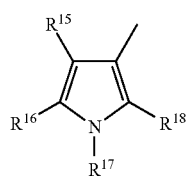
(A⁶)

wherein:
R¹⁵ is selected from the group consisting of a hydrogen atom; a halogen atom; a cyano; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different and $C_1$-$C_5$-halogenoalkyl comprising up to 9 halogen atoms that can be the same or different;
R¹⁶ and R¹⁸ are independently selected from the group consisting of a hydrogen atom; a halogen atom; substituted or non-substituted $C_1$-$C_5$-alkoxycarbonyl; substituted or non-substituted $C_1$-$C_5$-alkyl; $C_1$-$C_5$-halogenoalkoxy comprising up to 9 halogen atoms that can be the same or different and $C_1$-$C_5$-halogenoalkyl comprising up to 9 halogen atoms that can be the same or different;
R¹⁷ is selected from the group consisting of a hydrogen atom and substituted or non-substituted $C_1$-$C_5$-alkyl;

a heterocycle of formula (A⁷)

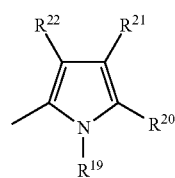
(A⁷)

wherein:
R¹⁹ is selected from the group consisting of a hydrogen atom and a $C_1$-$C_5$-alkyl
R²⁰, R²¹, and R²² are independently selected from the group consisting of a hydrogen atom; a halogen atom; substituted or non-substituted $C_1$-$C_5$-alkyl and $C_1$-$C_5$-halogenoalkyl comprising up to 9 halogen atoms that can be the same or different;

a heterocycle of formula (A⁸)

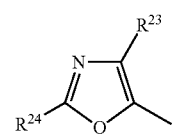
(A⁸)

wherein:
R²³ is selected from the group consisting of a hydrogen atom; a halogen atom; substituted or non-substituted $C_1$-$C_5$-alkyl and $C_1$-$C_5$-halogenoalkyl comprising up to 9 halogen atoms that can be the same or different;
R²⁴ is selected from the group consisting of a hydrogen atom or substituted or non-substituted $C_1$-$C_5$-alkyl and $C_1$-$C_5$-halogenoalkyl comprising up to 9 halogen atoms that can be the same or different;

a heterocycle of formula (A⁹)

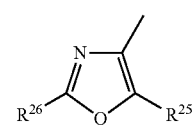
(A⁹)

wherein:
R²⁵ is selected from the group consisting of a hydrogen atom; a halogen atom; substituted or non-substituted $C_1$-$C_5$-alkyl and $C_1$-$C_5$-halogenoalkyl comprising up to 9 halogen atoms that can be the same or different;
R²⁶ is selected from the group consisting of a hydrogen atom; substituted or non-substituted $C_1$-$C_5$-alkyl and $C_1$-$C_5$-halogenoalkyl comprising up to 9 halogen atoms that can be the same or different;

a heterocycle of formula ($A^{10}$)

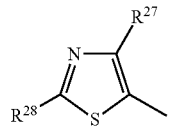

wherein:
- $R^{27}$ is selected from the group consisting of a hydrogen atom; a halogen atom; substituted or non-substituted $C_1$-$C_5$-alkyl and $C_1$-$C_5$-halogenoalkyl comprising up to 9 halogen atoms that can be the same or different;
- $R^{28}$ is selected from the group consisting of a hydrogen atom; a halogen atom; substituted or non-substituted $C_1$-$C_5$-alkyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino and substituted or non-substituted di($C_1$-$C_5$-alkyl)amino;

a heterocycle of formula ($A^{11}$)

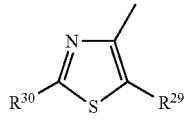

wherein:
- $R^{29}$ is selected from the group consisting of a hydrogen atom; a halogen atom; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different and $C_1$-$C_5$-halogenoalkyl comprising up to 9 halogen atoms that can be the same or different;
- $R^{30}$ is selected from the group consisting of a hydrogen atom; a halogen atom; substituted or non-substituted $C_1$-$C_5$-alkyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino and substituted or non-substituted di($C_1$-$C_5$-alkyl)amino;

a heterocycle of formula ($A^{12}$)

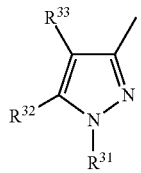

wherein:
- $R^{31}$ is selected from the group consisting of a hydrogen atom and a substituted or non-substituted $C_1$-$C_5$-alkyl
- $R^{32}$ is selected from the group consisting of a hydrogen atom; a halogen atom; substituted or non-substituted $C_1$-$C_5$-alkyl and $C_1$-$C_5$-halogenoalkyl comprising up to 9 halogen atoms that can be the same or different;
- $R^{33}$ is selected from the group consisting of a hydrogen atom; a halogen atom; a nitro; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different and $C_1$-$C_5$-halogenoalkyl comprising up to 9 halogen atoms that can be the same or different;

a heterocycle of formula ($A^{13}$)

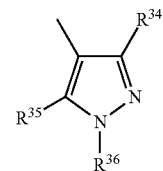

wherein:
- $R^{34}$ is selected from the group consisting of a hydrogen atom; a halogen atom; substituted or non-substituted $C_1$-$C_5$-alkyl; substituted or non-substituted $C_3$-$C_5$-cycloalkyl; $C_1$-$C_5$-halogenoalkyl comprising up to 9 halogen atoms that can be the same or different; substituted or non-substituted $C_1$-$C_5$-alkoxy; substituted or non-substituted $C_2$-$C_5$-alkynyloxy and $C_1$-$C_5$-halogenoalkoxy comprising up to 9 halogen atoms that can be the same or different;
- $R^{35}$ is selected from the group consisting of a hydrogen atom; a halogen atom; substituted or non-substituted $C_1$-$C_5$-alkyl; a cyano; substituted or non-substituted $C_1$-$C_5$-alkoxy; substituted or non-substituted $C_1$-$C_5$-alkylsulfanyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino and substituted or non-substituted di($C_1$-$C_5$-alkyl)amino;
- $R^{36}$ is selected from the group consisting of a hydrogen atom and substituted or non-substituted $C_1$-$C_5$-alkyl;

a heterocycle of formula ($A^{14}$)

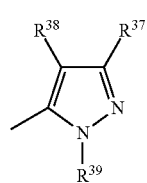

wherein:
- $R^{37}$ and $R^{38}$ are independently selected from the group consisting of a hydrogen atom; a halogen atom; substituted or non-substituted $C_1$-$C_5$; $C_1$-$C_5$-halogenoalkyl comprising up to 9 halogen atoms that can be the same or different; substituted or non-substituted $C_1$-$C_5$-alkoxy and a substituted or non-substituted $C_1$-$C_5$-alkylsulfanyl;
- $R^{39}$ is selected from the group consisting of a hydrogen atom and substituted or non-substituted $C_1$-$C_5$-alkyl;

a heterocycle of formula ($A^{15}$)

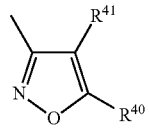
($A^{15}$)

wherein:
$R^{40}$ and $R^{41}$ are independently selected from the group consisting of a hydrogen atom; a halogen atom; substituted or non-substituted $C_1$-$C_5$-alkyl and $C_1$-$C_5$-halogenoalkyl comprising up to 9 halogen atoms that can be the same or different;

a heterocycle of formula ($A^{16}$)

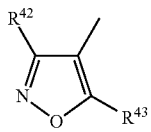
($A^{16}$)

wherein:
$R^{42}$ and $R^{43}$ are independently selected from the group consisting of a hydrogen atom; a halogen atom; substituted or non-substituted $C_1$-$C_5$-alkyl; and $C_1$-$C_5$-halogenoalkyl comprising up to 9 halogen atoms that can be the same or different or amino;

a heterocycle of formula ($A^{17}$)

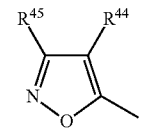
($A^{17}$)

wherein:
$R^{44}$ and $R^{45}$ are independently selected from the group consisting of a hydrogen atom; a halogen atom; substituted or non-substituted $C_1$-$C_5$-alkyl and $C_1$-$C_5$-halogenoalkyl comprising up to 9 halogen atoms that can be the same or different;

a heterocycle of formula ($A^{18}$)

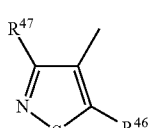
($A^{18}$)

wherein:
$R^{47}$ is selected from the group consisting of a hydrogen atom; a halogen atom; substituted or non-substituted $C_1$-$C_5$-alkyl and $C_1$-$C_5$-halogenoalkyl comprising up to 9 halogen atoms that can be the same or different;
$R^{46}$ is selected from the group consisting of a hydrogen atom; a halogen atom; substituted or non-substituted $C_1$-$C_5$-alkyl; $C_1$-$C_5$-halogenoalkyl comprising up to 9 halogen atoms that can be the same or different and substituted or non-substituted $C_1$-$C_5$-alkylsulfanyl;

a heterocycle of formula ($A^{19}$)

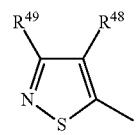
($A^{19}$)

wherein:
$R^{49}$ and $R^{48}$ are independently selected from the group consisting of a hydrogen atom; a halogen atom; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different and $C_1$-$C_5$-halogenoalkyl comprising up to 9 halogen atoms that can be the same or different;

a heterocycle of formula ($A^{20}$)

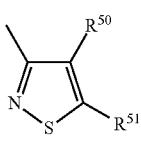
($A^{20}$)

wherein:
$R^{50}$ and $R^{51}$ are independently selected from the group consisting of a hydrogen atom; a halogen atom; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different and $C_1$-$C_5$-halogenoalkyl comprising up to 9 halogen atoms that can be the same or different;

a heterocycle of formula ($A^{21}$)

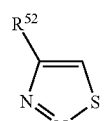
($A^{21}$)

wherein:
$R^{52}$ is selected from the group consisting of a hydrogen atom; a halogen atom; substituted or non-substituted $C_1$-$C_5$-alkyl and $C_1$-$C_5$-halogenoalkyl comprising up to 9 halogen atoms that can be the same or different;

a heterocycle of formula ($A^{22}$)

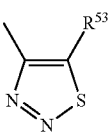
($A^{22}$)

wherein:
$R^{53}$ is selected from the group consisting of a hydrogen atom; a halogen atom; substituted or non-substituted $C_1$-$C_5$-alkyl and $C_1$-$C_5$-halogenoalkyl comprising up to 9 halogen atoms that can be the same or different;

a heterocycle of formula ($A^{23}$)

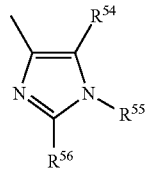

($A^{23}$)

wherein:
$R^{54}$ and $R^{56}$ are independently selected from the group consisting of a hydrogen atom; a halogen atom; substituted or non-substituted $C_1$-$C_5$-alkyl and $C_1$-$C_5$-halogenoalkyl comprising up to 9 halogen atoms that can be the same or different;

$R^{55}$ is selected from the group consisting of a hydrogen atom and substituted or non-substituted $C_1$-$C_5$-alkyl;

a heterocycle of formula ($A^{24}$)

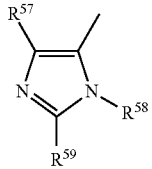

($A^{24}$)

wherein:
$R^{57}$ and $R^{59}$ are independently selected from the group consisting of a hydrogen atom; a halogen atom; substituted or non-substituted $C_1$-$C_5$-alkyl and $C_1$-$C_5$-halogenoalkyl comprising up to 9 halogen atoms that can be the same or different;

$R^{58}$ is selected from the group consisting of a hydrogen atom and substituted or non-substituted $C_1$-$C_5$-alkyl;

a heterocycle of formula ($A^{25}$)

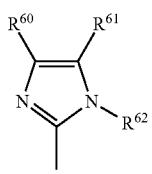

($A^{25}$)

wherein:
$R^{60}$ and $R^{61}$ are independently selected from the group consisting of a hydrogen atom; a halogen atom; substituted or non-substituted $C_1$-$C_5$-alkyl and $C_1$-$C_5$-halogenoalkyl comprising up to 9 halogen atoms that can be the same or different;

$R^{62}$ is selected from the group consisting of a hydrogen atom and substituted or non-substituted $C_1$-$C_5$-alkyl; and a heterocycle of formula ($A^{26}$)

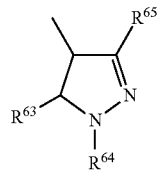

($A^{26}$)

wherein:
$R^{65}$ is selected from the group consisting of a hydrogen atom; a halogen atom; substituted or non-substituted $C_1$-$C_5$-alkyl; substituted or non-substituted $C_3$-$C_5$-cycloalkyl; $C_1$-$C_5$-halogenoalkyl comprising up to 9 halogen atoms that can be the same or different; substituted or non-substituted $C_1$-$C_5$-alkoxy; substituted or non-substituted $C_2$-$C_5$-alkynyloxy and $C_1$-$C_5$-halogenoalkoxy comprising up to 9 halogen atoms that can be the same or different;

$R^{63}$ is selected from the group consisting of a hydrogen atom; a halogen atom; substituted or non-substituted $C_1$-$C_5$-alkyl; a cyano; substituted or non-substituted $C_1$-$C_5$-alkoxy; substituted or non-substituted $C_1$-$C_5$-alkylsulfanyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino and di($C_1$-$C_5$-alkyl)amino;

$R^{64}$ is selected from the group consisting of a hydrogen atom and substituted or non-substituted $C_1$-$C_5$-alkyl.

3. The compound of claim 2 wherein A is selected from the group consisting of $A^2$; $A^6$; $A^{10}$ and $A^{13}$.

4. The compound of claim 3 wherein
A is $A^{13}$
wherein
$R^{34}$ is selected from the group consisting of a substituted or non-substituted $C_1$-$C_5$-alkyl, $C_1$-$C_5$-halogenoalkyl comprising up to 9 halogen atoms that can be the same or different; and substituted or non-substituted $C_1$-$C_5$-alkoxy;

$R^{35}$ is selected from the group consisting of a hydrogen atom and a halogen atom and $R^{36}$ is a substituted or non-substituted $C_1$-$C_5$-alkyl.

5. The compound of claim 1 wherein T is O.

6. The compound of claim 1 wherein n is 0, 1 or 2.

7. The compound of claim 1 wherein B is a 3-, 5-, 6- or 7-membered non aromatic carbocycle that can be substituted by one to four $C_1$-$C_8$-alkyl groups.

8. The compound of claim 7 wherein B is selected from the group consisting of cyclopropyl, cyclopentyl, cyclohexyl and cycloheptyl carbocycles that can be substituted by one to four methyl groups.

9. The compound of claim 1 wherein each X is independently selected from the group consisting of a halogen atom; substituted or non-substituted $C_1$-$C_8$-alkyl; $C_1$-$C_8$-halogenoalkyl comprising up to 9 halogen atoms that can be the same or different; substituted or non-substituted tri($C_1$-$C_8$-alkyl)silyl; substituted or non-substituted $C_1$-$C_8$-alkoxy and $C_1$-$C_8$-halogenoalkoxy comprising up to 9 halogen atoms that can be the same or different;

or wherein two consecutive substituents X together with the phenyl ring form a substituted or non substituted moiety selected from the group consisting of 1,3-benzodioxolyl;

1,2,3,4-tetrahydro-quinoxalinyl; 3,4-dihydro-2H-1,4-benzoxazinyl; 1,4-benzodioxanyl; indanyl; 2,3-dihydrobenzofuranyl; and indolinyl.

10. The compound of claim 1 wherein $Z^1$ and $Z^2$ are independently selected from the group consisting of a hydrogen atom and a substituted or non-substituted $C_1$-$C_8$-alkyl.

11. The compound of claim 1 wherein $Z^3$ is selected from the group consisting of a non-substituted $C_3$-$C_7$ cycloalkyl and a $C_3$-$C_7$ cycloalkyl substituted by up to 10 substituents independently selected from the group consisting of halogen atoms, $C_1$-$C_8$-alkyl, $C_1$-$C_8$-halogenoalkyl comprising up to 9 halogen atoms that can be the same or different, $C_1$-$C_8$-alkoxy and $C_1$-$C_8$-halogenoalkoxy comprising up to 9 halogen atoms that can be the same or different.

12. The compound of claim 1 wherein $Z^3$ is a non-substituted $C_3$-$C_7$-cycloalkyl.

13. The compound of claim 1 wherein $Z^4$ and $Z^5$ are independently selected from the group consisting of a hydrogen atom, a halogen atom and a substituted or non-substituted $C_1$-$C_8$-alkyl.

14. The compound of claim 1 wherein each R is independently selected from the group consisting of a hydrogen atom; halogen atom; cyano; substituted or non-substituted $C_1$-$C_8$-alkylamino; substituted or non-substituted di-$C_1$-$C_8$-alkylamino; substituted or non-substituted tri($C_1$-$C_8$-alkyl)silyl; substituted or non-substituted $C_1$-$C_8$-alkyl; $C_1$-$C_8$-halogenoalkyl comprising up to 9 halogen atoms that can be the same or different; substituted or non-substituted $C_1$-$C_8$-alkoxy; $C_1$-$C_8$-halogenoalkoxy comprising up to 9 halogen atoms that can be the same or different; substituted or non-substituted $C_1$-$C_8$-alkylsulfanyl; amino; hydroxyl; nitro; substituted or non-substituted $C_1$-$C_8$-alkoxycarbonyl; and substituted or non-substituted $C_2$-$C_8$-alkynyloxy.

15. A fungicide composition comprising, as an active ingredient, an effective amount of the compound of claim 1 and an agriculturally acceptable support, carrier or filler.

16. A compound of formula (II)

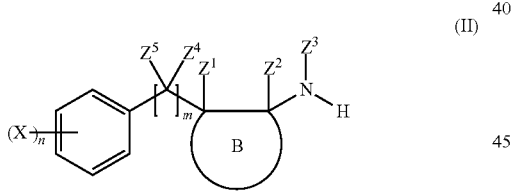

(II)

wherein,
each X is selected from the group consisting of a halogen atom; nitro; cyano; isonitrile; hydroxy; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-halogenoalkyl having 1 to 5 halogen atoms; substituted or non-substituted $C_2$-$C_8$-alkenyl; $C_2$-$C_8$-halogenoalkenyl having 1 to 5 halogen atoms; substituted or non-substituted $C_2$-$C_8$-alkynyl; $C_2$-$C_8$-halogenoalkynyl having 1 to 5 halogen atoms; substituted or non-substituted $C_1$-$C_8$-alkoxy; $C_1$-$C_8$-halogenoalkoxy having 1 to 5 halogen atoms; substituted or non-substituted $C_1$-$C_8$-alkylsulfanyl; $C_1$-$C_8$-halogenoalkylsulfanyl having 1 to 5 halogen atoms; substituted or non-substituted $C_1$-$C_8$-alkylsulfinyl; $C_1$-$C_8$-halogenoalkylsulfinyl having 1 to 5 halogen atoms; substituted or non-substituted $C_1$-$C_8$-alkylsulfonyl; $C_1$-$C_8$-halogenoalkylsulfonyl having 1 to 5 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-halogenoalkenyloxy having 1 to 5 halogen atoms; substituted or non-substituted $C_3$-$C_8$-alkynyloxy; $C_2$-$C_8$-halogenoalkynyloxy having 1 to 5 halogen atoms; substituted or non-substituted $C_3$-$C_7$-cycloalkyl; $C_3$-$C_7$-halogenocycloalkyl having 1 to 5 halogen atoms; substituted or non-substituted ($C_3$-$C_7$-cycloalkyl)-$C_1$-$C_8$-alkyl; substituted or non-substituted ($C_3$-$C_7$-cycloalkyl)-$C_1$-$C_8$-alkenyl; substituted or non-substituted ($C_3$-$C_7$-cycloalkyl)-$C_2$-$C_8$-alkynyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted $C_1$-$C_8$-alkylcarbonyl; $C_1$-$C_8$-halogenoalkylcarbonyl having 1 to 5 halogen atoms; substituted or non-substituted $C_1$-$C_8$-alkylcarbonyloxy; $C_1$-$C_8$-halogenoalkylcarbonyloxy having 1 to 5 halogen atoms; substituted or non-substituted $C_1$-$C_8$-alkylcarbonylamino; $C_1$-$C_8$-halogenoalkyl-carbonylamino having 1 to 5 halogen atoms; substituted or non-substituted $C_1$-$C_8$-alkoxycarbonyl; $C_1$-$C_8$-halogenoalkoxycarbonyl having 1 to 5 halogen atoms; substituted or non-substituted $C_1$-$C_8$-alkyloxycarbonyloxy; $C_1$-$C_8$-halogenoalkoxycarbonyloxy having 1 to 5 halogen atoms; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl that can be substituted by up to 6 groups Q; $C_1$-$C_8$-arylalkyl that can be substituted by up to 6 groups Q; $C_2$-$C_8$-arylalkenyl that can be substituted by up to 6 groups Q; $C_2$-$C_8$-arylalkynyl that can be substituted by up to 6 groups Q; aryloxy that can be substituted by up to 6 groups Q arylsulfanyl that can be substituted by up to 6 groups Q; arylamino that can be substituted by up to 6 groups Q; $C_1$-$C_8$-arylalkyloxy that can be substituted by up to 6 groups Q; $C_1$-$C_8$-arylalkylsulfanyl that can be substituted by up to 6 groups Q; and $C_1$-$C_8$-arylalkylamino that can be substituted by up to 6 groups Q;

n is 0, 1, 2, 3, 4 or 5;
m is 0 or 1;
or two substituents X together with the consecutive carbon atoms to which they are linked can form a 5- or 6-membered, saturated carbocycle or saturated heterocycle, which can be substituted by up to four groups Q that can be the same or different;

$Z^1$ and $Z^2$ are independently selected from the group consisting of a hydrogen atom; a halogen atom; cyano; a substituted or non-substituted $C_1$-$C_8$-alkyl; $C_1$-$C_8$-halogenoalkyl having 1 to 5 halogen atoms; substituted or non-substituted $C_1$-$C_8$-alkoxy; substituted or non-substituted $C_1$-$C_8$-alkylsulfanyl; and substituted or non-substituted $C_1$-$C_8$-alkoxycarbonyl;

$Z^3$ is selected from the group consisting of a non-substituted $C_3$-$C_7$-cycloalkyl and a $C_3$-$C_7$-cycloalkyl substituted by up to 10 substituents independently selected from the group consisting of halogen atoms, cyano, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl and di-$C_1$-$C_8$-alkylamino-carbonyl;

$Z^4$ and $Z^5$ are independently selected from the group consisting of a hydrogen atom; a halogen atom; cyano; a substituted or non-substituted $C_1$-$C_8$-alkyl; $C_1$-$C_8$-halogenoalkyl having 1 to 5 halogen atoms; substituted or non-substituted $C_1$-$C_8$-alkoxy; substituted or non-substituted $C_1$-$C_8$-alkylsulfanyl; and substituted or non-substituted $C_1$-$C_8$-alkoxycarbonyl;

or $Z^4$ and $Z^5$ are a $C_2$-$C_5$-alkylene group that can be substituted by one to four $C_1$-$C_8$-alkyl groups;

each Q is independently selected from the group consisting of a halogen atom; cyano; nitro; substituted or non-substituted $C_1$-$C_8$-alkyl; $C_1$-$C_8$-halogenoalkyl having 1 to 9 halogen atoms that can be the same or different; substituted or non-substituted $C_1$-$C_8$-alkoxy; $C_1$-$C_8$-halogenoalkoxy having 1 to 9 halogen atoms that can be the same or different; substituted or non-substituted $C_1$-$C_8$-alkylsulfanyl; $C_1$-$C_8$-halogenoalkylsulfanyl having 1 to 9 halogen atoms that can be the same or different; substituted or non-substituted tri($C_1$-$C_8$)alkylsilyl; substituted or non-substituted tri($C_1$-$C_8$)alkylsilyl-$C_1$-$C_8$-alkyl; substituted or non-substituted ($C_1$-$C_8$-alkoxyimino)-$C_1$-$C_8$-alkyl; and substituted or non-substituted (benzyloxyimino)-$C_1$-$C_8$-alkyl; and B is selected from the group consisting of cyclopropyl, cyclobutyl, cyclopentyl, cyclohexyl and cycloheptyl moieties with the exclusion of N-cyclopropyl-2-phenyl-cyclohexanamine.

17. A method for controlling phytopathogenic fungi of crops comprising applying an agronomically effective and substantially non-phytotoxic quantity of the compound of claim 1 to the soil where plants grow or are capable of growing, to the leaves and/or the fruit of plants or to the seeds of plants.

18. A method for controlling phytopathogenic fungi of crops comprising applying an agronomically effective and substantially non-phytotoxic quantity of the composition of claim 15 to the soil where plants grow or are capable of growing, to the leaves and/or the fruit of plants or to the seeds of plants.

19. The compound of claim 12 wherein $Z^3$ is non-substituted cyclopropyl.

* * * * *